(12) United States Patent
Nanaumi

(10) Patent No.: US 9,737,216 B2
(45) Date of Patent: Aug. 22, 2017

(54) OBJECT INFORMATION ACQUIRING APPARATUS AND METHOD FOR CONTROLLING OBJECT INFORMATION ACQUIRING APPARATUS

(71) Applicant: CANON KABUSHIKI KAISHA, Tokyo (JP)

(72) Inventor: Ryuichi Nanaumi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 245 days.

(21) Appl. No.: 14/303,726

(22) Filed: Jun. 13, 2014

(65) Prior Publication Data

US 2014/0378811 A1 Dec. 25, 2014

(30) Foreign Application Priority Data

Jun. 21, 2013 (JP) .................................. 2013-130500
May 30, 2014 (JP) .................................. 2014-113149

(51) Int. Cl.
*A61B 5/00* (2006.01)
*G01N 21/17* (2006.01)

(52) U.S. Cl.
CPC .......... *A61B 5/0095* (2013.01); *A61B 5/0075* (2013.01); *G01N 21/1702* (2013.01);
(Continued)

(58) Field of Classification Search
CPC ............... A61B 5/0075; A61B 5/0095; G01N 2021/1706; G01N 2021/1708; G01N 21/1702
See application file for complete search history.

(56) References Cited

U.S. PATENT DOCUMENTS 5,694,938 A * 12/1997 Feng .................... A61B 5/0073
600/425
8,144,327 B2 3/2012 Nakajima et al. ............ 356/432
(Continued)

FOREIGN PATENT DOCUMENTS

JP H07-159239 6/1995
JP 2002-139420 5/2002
(Continued)

OTHER PUBLICATIONS

Chinese Office Action issued Dec. 1, 2015 in counterpart P.R. China patent application CN 201410279140.7.
(Continued)

*Primary Examiner* — Katherine Fernandez
(74) *Attorney, Agent, or Firm* — Fitzpatrick, Cella, Harper & Scinto

(57) ABSTRACT

An object information acquiring apparatus comprises a light irradiation unit that irradiates an object with pulsed light; a probe that converts an acoustic wave generated in the object due to first pulsed light into an acoustic wave signal; a photo-detection unit that converts second pulsed light propagated through the object into an optical signal; a frequency analysis unit that acquires a background optical coefficient with respect to the inside of the object on the basis of a predetermined frequency component of the optical signal; a light intensity acquiring unit that acquires a distribution of light intensity of the first pulsed light reaching the inside of the object using the background optical coefficient; and an information acquiring unit that acquires object information, using the acoustic wave signal and the distribution of light intensity.

16 Claims, 20 Drawing Sheets

(52) U.S. Cl.
CPC ............. *G01N 2021/1706* (2013.01); *G01N 2021/1708* (2013.01)

(56) References Cited

U.S. PATENT DOCUMENTS

| | | | |
|---|---|---|---|
| 2006/0192965 A1* | 8/2006 | Tromberg | A61B 5/0059 356/432 |
| 2010/0331707 A1* | 12/2010 | Fukutani | A61B 5/0073 600/476 |
| 2011/0172513 A1 | 7/2011 | Nakajima et al. | 600/407 |
| 2011/0224931 A1 | 9/2011 | Yoshimoto et al. | 702/71 |
| 2013/0109941 A1* | 5/2013 | Li | G01N 21/1702 600/364 |
| 2014/0135610 A1 | 5/2014 | Nanaumi | 600/407 |
| 2014/0303473 A1 | 10/2014 | Nanaumi | 600/407 |

FOREIGN PATENT DOCUMENTS

| | | |
|---|---|---|
| WO | WO 2010/030043 | 3/2010 |
| WO | WO 2010/061673 | 6/2010 |
| WO | WO 2012/153665 | 11/2012 |

OTHER PUBLICATIONS

K. Suzuki et al., "Quantitative Measurement of Optical Parameters in Normal Breasts Using Time-Resolved Spectroscopy: in vivo Results of 30 Japanese Women", *Journal of Biomedical Optics*, vol. 1, No. 3, pp. 330-334 (Jul. 1996).
EESR issued Dec. 18, 2014 in counterpart EPA 14172279.3.

\* cited by examiner

OBJECT INFORMATION ACQUIRING APPARATUS AND METHOD FOR CONTROLLING OBJECT INFORMATION ACQUIRING APPARATUS

BACKGROUND OF THE INVENTION

Field of the Invention

The present invention relates to an object information acquiring apparatus that acquires information on the inside of an object.

Description of the Related Art

Attempts have been made to noninvasively acquire information on the inside of a living body using light. For example, when a living body that is an object is irradiated with measurement light such as pulsed laser light, an acoustic wave is generated when the measurement light is absorbed by the biological tissue in the object. Information on the inside of the living body can be acquired by receiving and analyzing the acoustic wave (typically an ultrasound wave). Such a technique is referred to as photoacoustic imaging.

The photoacoustic imaging implements imaging of information related to an absorption coefficient with respect to the inside of the object. The absorption coefficient is the rate at which the biological tissue absorbs light energy. Measuring the absorption coefficient allows acquisition of the concentrations of components of the biological tissue. In particular, the use of light with a wavelength likely to be absorbed by hemoglobin in the blood enables the concentration ratio of oxyhemoglobin to deoxyhemoglobin to be determined. This allows the oxygen saturation of the biological tissue to be calculated. As is known, if a tumor tissue is present in the living body, the oxygen saturation decreases in the corresponding site. Thus, diagnosis for tumor is expected to be enabled by measuring the absorption coefficient.

Now, a method for calculating the absorption coefficient with respect to the inside of the living body based on the received acoustic wave will be described. First, the received acoustic wave is reconstructed to generate a distribution of initial sound pressure of a sound source. The initial sound pressure can be expressed by multiplying the intensity of light having reached a target area, the absorption coefficient of the light, and a Grueneisen constant together. That is, the distribution of the absorption coefficient can be obtained by dividing the distribution of initial sound pressure by the Grueneisen constant and by the distribution of the light intensity.

When the object is a living body, the distribution of light intensity needs to be determined in order to obtain the absorption coefficient because the Grueneisen constant is considered to be a known predetermined value. The distribution of light intensity can be calculated based on the optical characteristics of the biological tissue. The biological tissue has two optical characteristics: a light absorption characteristic (hereinafter referred to as a background absorption coefficient) and a light scattering characteristic (background scattering coefficient) for an area through which the light passes after being provided to the object and before reaching the light absorber. The two coefficients are collectively referred to as a background optical coefficient. The background optical coefficient significantly affects the calculation of the absorption coefficient and thus needs to have an accurate value.

The background optical coefficient can be measured by irradiating the object with measurement light and detecting light having propagated through the object. For example, Japanese Patent Application Laid-open No. 2002-139420 and Non-Patent Document 1 describe apparatuses that measure the background optical coefficient using a time resolved measurement method based on pulsed light. Furthermore, Japanese Patent Application Laid-open No. H07-159239 describes an apparatus that measures the background optical coefficient using a phase modulation measurement method based on intensity modulated light.

Non-Patent Literature 1: "Quantitative measurement of optical parameters in normal breasts using time-resolved spectroscopy: in vivo results of 30 Japanese women", Kazunori Suzuki M.D.; Yutaka Yamashita; Kazuyoshi Ohta; Masao Kaneko; Masayuki Yoshida M.D.; Britton Chance, Journal of Biomedical Optics 1(03), pp. 330-334

SUMMARY OF THE INVENTION

To allow measurement of the background optical coefficient of a particular object, the object needs to be irradiated with measurement light. However, a light source used for photoacoustic imaging and a light source used to measure the background optical coefficient have different desired characteristics. Thus, using a common light source both for photoacoustic imaging and for the measurement is difficult.

For example, the light source used for normal photoacoustic imaging is pulsed light with a pulse width of several tens of nanoseconds to several hundred nanoseconds. However, such time resolved measurement as described in Japanese Patent Application Laid-open No. 2002-139420 needs irradiation with light with a pulse width of several tens of picoseconds to several hundred picoseconds. Furthermore, such phase modulation measurement as described in Japanese Patent Application Laid-open No. H07-159239 needs irradiation of intensity modulated light instead of the pulsed light. Thus, when an attempt is made to measure the background optical coefficient in a photoacoustic imaging apparatus, the apparatus needs to be provided with different light sources and is disadvantageously complicated.

With these problems of the conventional technique in view, it is an object of the present invention to provide an object information acquiring apparatus that allows photoacoustic measurement and measurement of the background optical coefficient to be performed using a common light source.

The present invention in its one aspect provides an object information acquiring apparatus comprises a light irradiation unit that irradiates an object with pulsed light; an acoustic wave probe configured to convert an acoustic wave generated in the object due to first pulsed light from the light irradiation unit into an acoustic wave signal; a photo-detection unit configured to convert second pulsed light, which is from the light irradiation unit and propagated through the object, into an optical signal; a frequency analysis unit configured to acquire a background optical coefficient with respect to the inside of the object on the basis of a predetermined frequency component of the optical signal; a light intensity acquiring unit configured to acquire a distribution of light intensity that is a distribution of an intensity of the first pulsed light reaching the inside of the object on the basis of the background optical coefficient; and an information acquiring unit configured to acquire object information on the inside of the object, on the basis of the acoustic wave signal and the distribution of light intensity.

The present invention in its another aspect provides a method for acquiring information on an inside of an object, the method comprises a step of irradiating the object with first pulsed light; a step of converting an acoustic wave generated in the object due to the first pulsed light into an acoustic wave signal; a step of irradiating the object with second pulsed light; a step of converting the second pulsed light propagated through the object into an optical signal; a step of acquiring a background optical coefficient with respect to the inside of the object on the basis of a predetermined frequency component of the optical signal; a light intensity acquiring step of acquiring, on the basis of the background optical coefficient, a distribution of light intensity that is a distribution of an intensity of the first pulsed light reaching the inside of the object; and a step of acquiring object information on the inside of the object, on the basis of the acoustic wave signal and the distribution of light intensity.

According to the present invention, an object information acquiring apparatus can be obtained that is capable of photoacoustic measurement and background optical coefficient measurement by means of a common light source.

Further features of the present invention will become apparent from the following description of exemplary embodiments with reference to the attached drawings.

DESCRIPTION OF THE EMBODIMENTS

Figure 1:
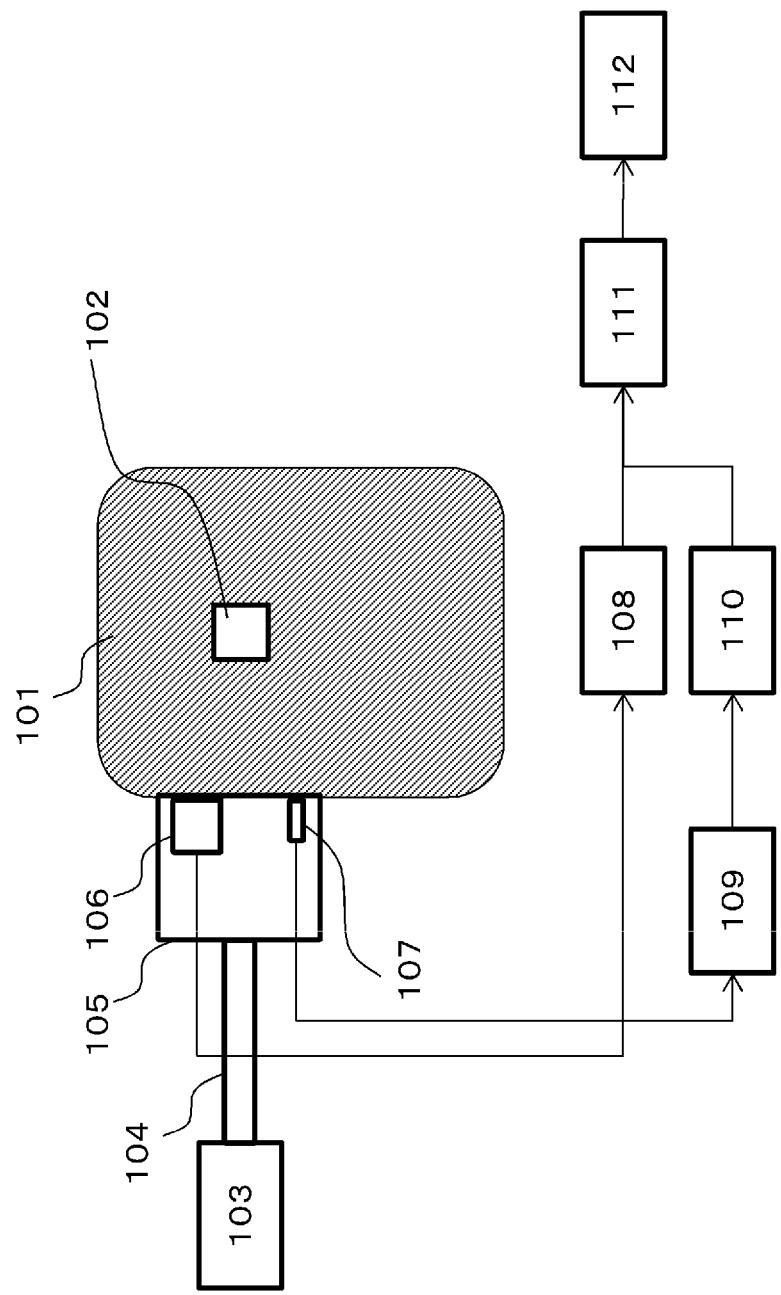
FIG. 1 is a diagram showing a configuration of an object information acquiring apparatus according to a first embodiment.

Embodiments of the present invention will be described below in detail with reference to the drawings. The same components are in principle denoted by the same reference numerals, and duplicate descriptions are omitted. Numerical values, materials, and the like used in the description of the embodiments are not intended to limit the scope of the invention. Object information as used herein refers to information based on the distribution of an absorption coefficient with respect to the inside of an object. The object information includes the distribution of the absorption coefficient and the distribution of concentrations of substances providing the object, such as the distribution of oxygen saturation, which is determined from the absorption coefficient.

First Embodiment

A photoacoustic measurement apparatus according to a first embodiment of the present invention is an apparatus that irradiates the object with pulsed light to analyze a photoacoustic wave generated in the object due to the pulsed light, allowing imaging of the distribution of the absorption coefficient inside the living body, which is the object. Furthermore, the photoacoustic measurement apparatus has a function to measure a background optical coefficient for the object using the pulsed light in order to acquire the distribution of light intensity needed to calculate the absorption coefficient. First, components of the apparatus will be described. Then, a processing method performed by the apparatus will be described. Finally, effects of the apparatus will be described.

<System Configuration>

First, with reference to FIG. 1, a configuration of the photoacoustic measurement apparatus according to a first embodiment will be described. The photoacoustic measurement apparatus according to the first embodiment includes a light source 103, a light guiding unit 104, a measurement unit 105, a reconstruction unit 108, a frequency analysis unit 109, a light intensity acquiring unit 110, an information acquiring unit 111, and a display unit 112. Furthermore, the measurement unit 105 incorporates an acoustic wave probe 106 and a photodetector 107. In FIG. 1, a living body that is an object is denoted by reference numeral 101. A target area for photoacoustic measurement (hereinafter referred to as an region of interest) is denoted by reference numeral 102.

<<Light Source 103>>

The light source 103 is an apparatus that generates pulsed light. The intensity of a photoacoustic signal is proportional to the intensity of light, and thus the power of the light source is preferably high. For example, a high-power pulsed laser light source such as a titanium sapphire laser or an alexandrite laser can be suitably used. Furthermore, an incoherent light source such as a light emitting diode or a flash lamp may be used as the light source 103. Additionally, light generated by the light source 103 preferably has a pulse width of approximately 400 picoseconds to 650 nanoseconds. Alternatively, the pulse width of the light generated by the light source 103 may fall within the range from 10 nanoseconds to 650 nanoseconds, which is commonly used for photoacoustic imaging and which is unsuitable for time resolved measurement. Moreover, the pulse width of the light generated by the light source 103 may fall within the range from 100 nanoseconds to 650 nanoseconds.

The light source 103 enables to generate the first pulsed light for photoacoustic measurement and the second pulsed light for measurement of the background optical coefficient. The first pulsed light for photoacoustic measurement and the second pulsed light for measurement of the background optical coefficient, generated by the same light source 103, have substantially same waveform. The emission interval of the pulsed light can preferably be set differently for the photoacoustic measurement and for measurement of the background optical coefficient.

The emission interval of the pulsed light for the photoacoustic measurement is preferably as short as possible but needs to be longer than a time needed for an acoustic wave probe to detect an acoustic wave during at least a single pulsed light irradiation. Furthermore, the emission interval of the pulsed light for measurement of the background optical coefficient is similarly preferably as short as possible but needs to be at least longer than the sum of the pulse width and the extent of the temporal waveform by the response of the object. When the object 101 is a living body, the extent of the temporal waveform may be assumed to be about 10 nanoseconds.

<<Light Guiding Unit 104>>

The light guiding unit 104 is a unit that guides the pulsed light generated by the light source 103 to the measurement unit 105. The light guiding unit 104 is formed of an optical member such as optical elements, optical fibers, a mirror, or a prism. When light is guided using optical fibers, a bundle fiber is preferably used which provides both transmission of a large intensity of light and flexibility.

<<Measurement Unit 105>>

The measurement unit 105 is connected to the light guiding unit 104 and incorporates an acoustic wave probe and a photodetector. The pulsed light provided by the measurement unit 105 allows photoacoustic measurement and measurement of the background optical coefficient of the object. The measurement unit 105 uses the acoustic wave probe 106 to receive an acoustic wave in performing photoacoustic measurement and uses the photodetector 107 to detect the pulsed light having propagated through the object in measuring the background optical coefficient.

The light irradiation section 103, the light guiding unit 104, and a part of the measurement unit 105 provide a light irradiation unit according to the present invention.

Furthermore, the measurement unit 105 enables the irradiation area of the pulsed light with which the object is irradiated to be changed in two stages. For photoacoustic measurement, the measurement unit 105 provides light over a large area in order to allow a photoacoustic wave to be generated over a large area inside the object. When measuring the background optical coefficient, the measurement unit 105 provides light within a small area in order to suppress rounding of the waveform of the detected pulsed light.

Figure 2A:
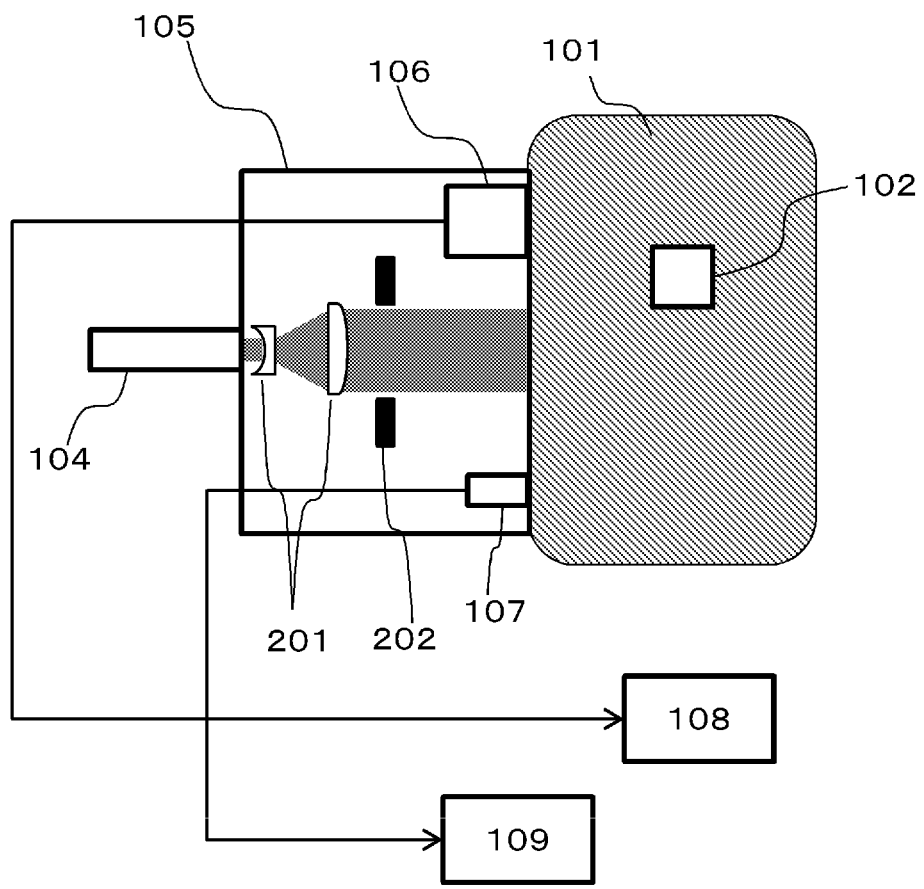
FIGS. 2A to 2C are detailed diagrams showing a configuration of a measurement unit according to the first embodiment.
Figure 2B:
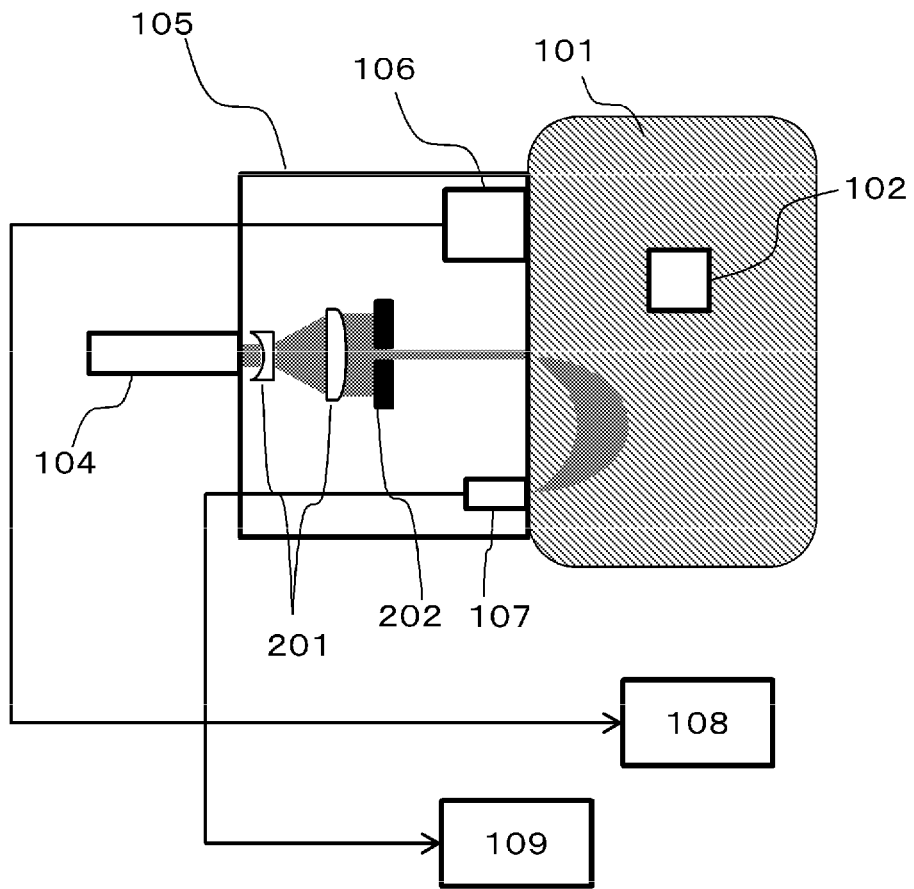

A specific method for changing the irradiation area of the pulsed light will be described with reference to FIGS. 2A to 2C. FIGS. 2A and 2B show examples in which the irradiation area is changed using an optical diaphragm.

In FIGS. 2A and 2B, a beam expander is denoted by reference numeral 201 and is an optical member that enlarges light emitted by the light guiding unit 104. An optical diaphragm 202 is opened for photoacoustic measurement and closed for measurement of the background optical coefficient. Thus, the pulsed light can be provided to the object 101 over an area suitable for each measurement. The optical diaphragm 202 may be located midway between the light guiding unit 104 and the beam expander 201.

Figure 2C:
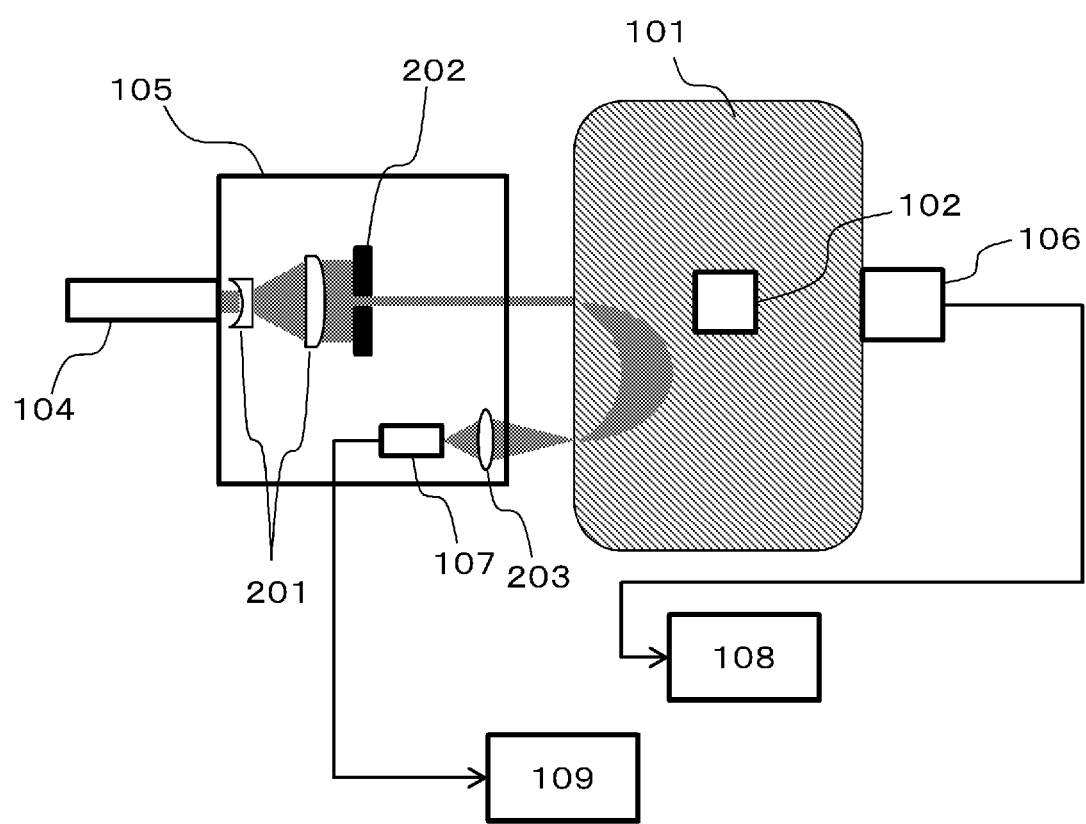

FIG. 2C shows an example in which the measurement unit 105 is located away from the object 101. The photodetector 203 preferably detects light within a small area for the same reason why the pulsed light is provided within a small area. Thus, when the measurement unit is located away from the object, a lens 203 may be installed which brings the photodetector 107 and a surface of the object 101 into optically conjugate relations. This provides a space in which, for example, a holding member allowing the object 101 to be held is located.

Figure 3A:
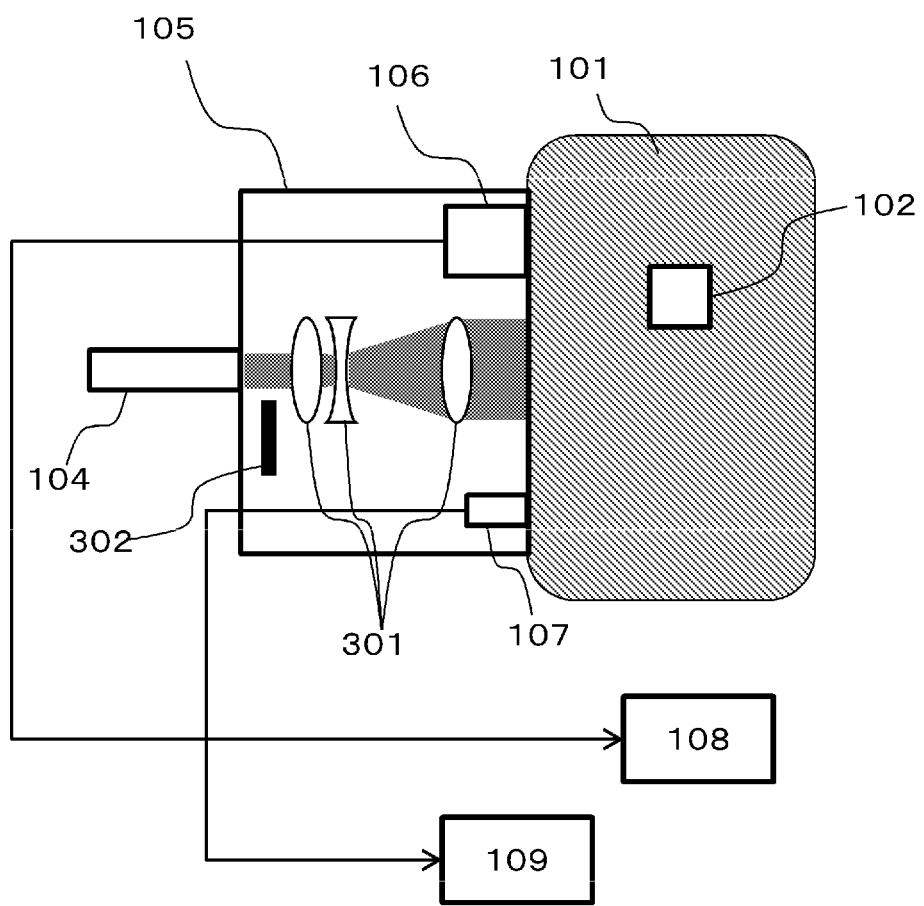
FIGS. 3A and 3B are detailed diagrams showing a configuration of a measurement unit according to the first embodiment.
Figure 3B:
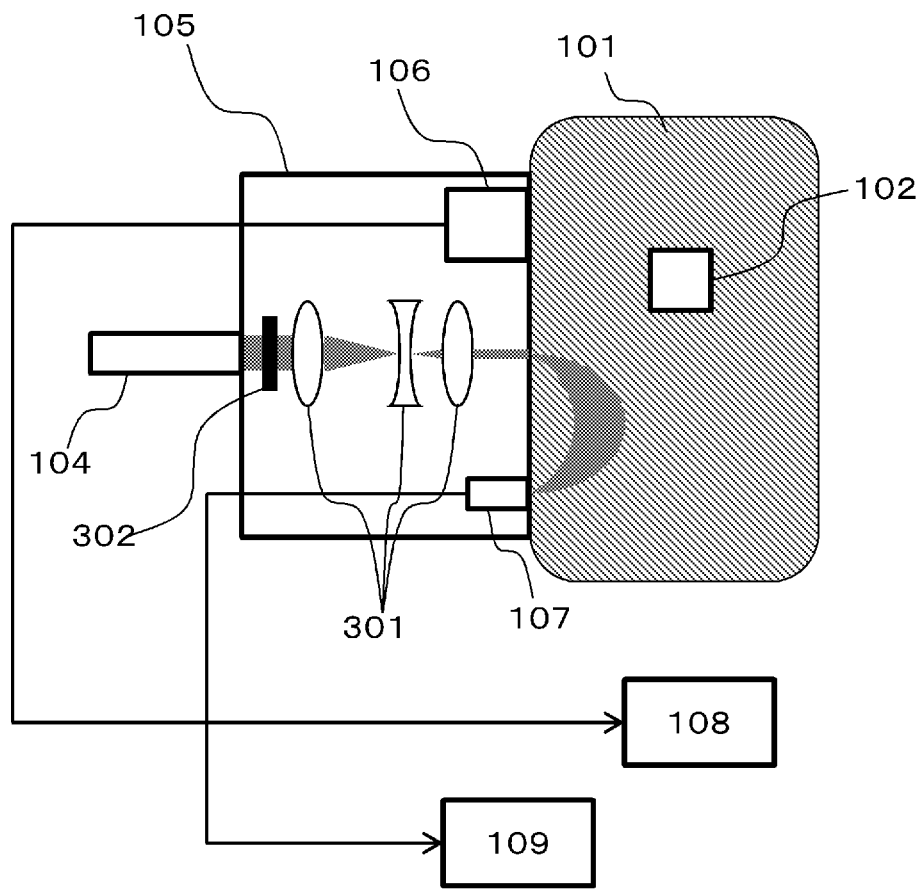

FIGS. 3A and 3B show an example in which the irradiation area is changed using a variable beam expander (reference numeral 301). The variable beam expander 301 switches the irradiation area of the pulsed light by being arranged as shown in FIG. 3A in order to receive a photoacoustic wave and being arranged as shown in FIG. 3B in order to detect propagating light. In the example shown in FIG. 3B, the light is focused and the intensity per area is increased, and thus, a neutral density filter 302 is interposed in the apparatus. This enables suppression of an increase in the intensity per area of the pulsed light with which the object 101 is irradiated.

The examples shown in FIGS. 2A to 2C and FIGS. 3A and 3B allow the irradiation area of the pulsed light to be switched without moving an optical axis. This configuration enables a reduction in the size of the measurement unit 105.

Figure 4A:
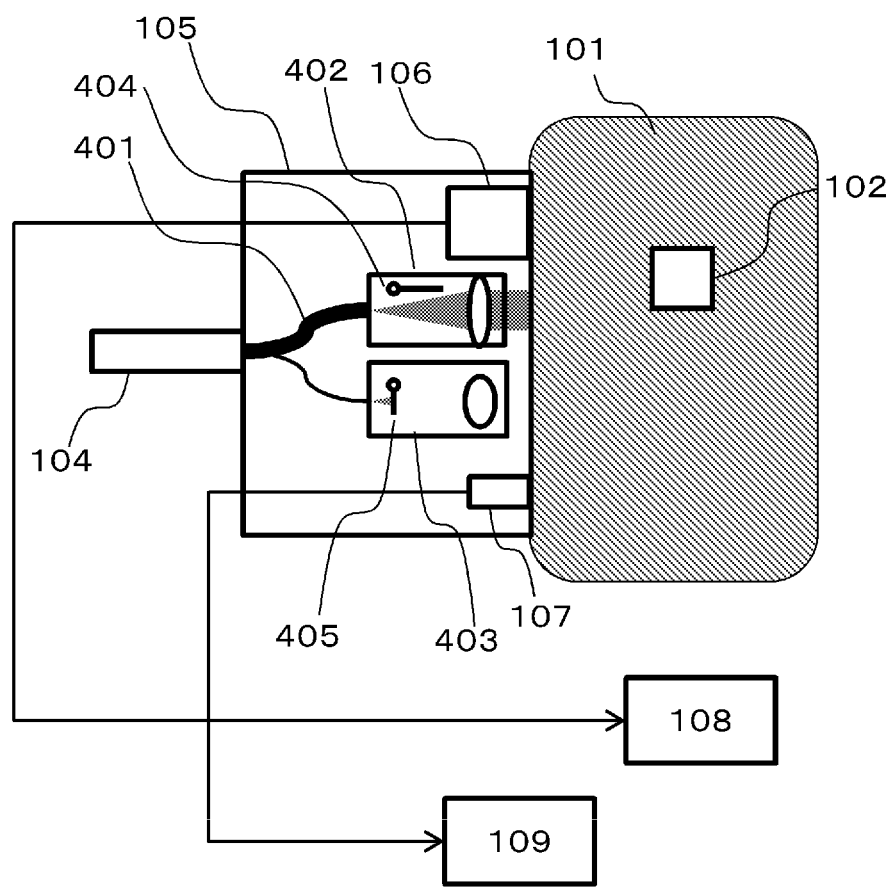
FIGS. 4A and 4B are detailed diagrams showing a configuration of a measurement unit according to the first embodiment.
Figure 4B:
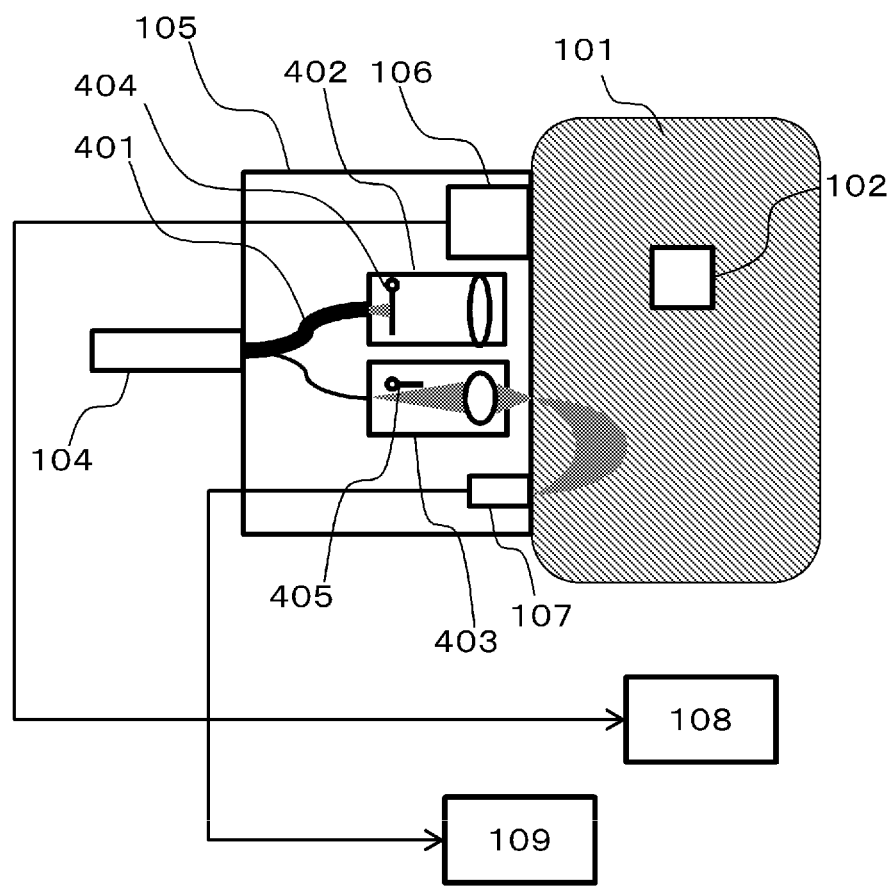

FIGS. 4A and 4B show an example in which two optical systems are provided and switched to each other to change the irradiation area of the pulsed light. FIG. 4A shows a case of photoacoustic measurement, and FIG. 4B shows a case of measurement of the background optical coefficient. Pulsed light emitted by the light guiding unit 104 is divided into two beams by a branch unit 401. The branch unit 401 may be an optical element such as optical fibers or a beam splitter.

One of the beams resulting from the branching is provided via a first irradiation unit 402 to the object 101 over a large area. The other beam is provided via a second irradiation unit 403 to the object 101 within a small area. The first irradiation unit 402 and the second irradiation unit 403 have a first shading unit 404 and a second shading unit 405, respectively. When one of the first and second irradiation units 402 and 403 is open, the other is closed. Thus, irradiation light beams from the first and second irradiation units 402 and 403 can be prevented from mutually affecting the measurement.

<<Acoustic Wave Probe 106>>

The acoustic wave probe 106 is a unit that converts an acoustic wave generated inside the object into an analog electric signal. The analog electric signal into which the acoustic wave probe 106 converts the acoustic wave is hereinafter referred to as an acoustic wave signal. The acoustic wave probe is also referred to simply as a probe or as an acoustic wave detector or a transducer. The acoustic wave as used herein is typically an ultrasound wave and includes elastic waves referred to as a sound wave, an ultrasound wave, a photoacoustic wave, and a light-induced ultrasound wave. The acoustic wave probe 106 may include a single acoustic wave probe or a plurality of acoustic wave probes. Furthermore, the acoustic wave probe 106 may be located inside the measurement unit 105 or outside the measurement unit 105 as shown in FIG. 2C.

Furthermore, desirably, the acoustic wave probe 106 is sensitive and has a wide frequency band. Specifically, the acoustic wave probe 106 may be piezoelectric ceramics (PZT), polyvinylidene fluoride resin (PVDF), capacitive micromachined ultrasound transducer (CMUT), or a Fabry-Perot interferometer. However, the present invention is not limited to these acoustic wave probes but any acoustic wave probe may be used provided that the acoustic wave probe accomplishes the functions of a probe.

Additionally, the acoustic wave probe 106 may include a plurality of one- or two-dimensionally arranged reception elements. The use of multi-dimensionally arranged elements allows acoustic waves to be simultaneously received at a plurality of locations. This enables a reduction in measurement time and in adverse effects such as vibration of the object. When the probe is smaller than the object, the probe may be scanned to receive acoustic waves at a plurality of positions.

<<Photodetector 107>>

The photodetector 107 is a unit that detects pulsed light emitted by the measurement unit 105 and propagated through the object 101 to generate an optical signal. The optical signal is an electric signal representing the transition of the intensity of detected light in a time series manner. An acquired signal itself is hereinafter referred to as an optical signal, and a waveform expressed by the optical signal is hereinafter referred to as a temporal waveform.

The photodetector 107 may be a photomultiplier tube (PMT), avalanche photodiode (APD), a photodiode (PD), or the like. A generated optical signal is output to the frequency analysis unit 109.

<<Reconstruction Unit 108>>

The reconstruction unit 108 is a unit that executes an image reconstruction process based on an acoustic wave signal generated by the acoustic wave probe 106 to generate a distribution of initial sound pressure in the region of interest 102.

Specifically, the reconstruction unit 108 amplifies and converts the acoustic wave signal generated by the acoustic wave probe 106 into a digital signal and then executes the image reconstruction process. Any of the following known processing methods may be adopted as the image reconstruction method: a method for back projection in a time domain, a reconstruction method based on time reversal, a method for reconstruction in a Fourier domain, and a model-based reconstruction method. The generated distribution of initial sound pressure is output to the information acquiring unit 111.

<<Frequency Analysis Unit 109>>

The frequency analysis unit 109 is a unit that converts the optical signal generated by the photodetector 107 into a predetermined frequency component and that calculates a background optical coefficient for the object, that is, a background absorption coefficient and a background scattering coefficient, using the amplitude decay and phase difference of the frequency component.

Specifically, the frequency analysis unit 109 converts the optical signal into a frequency domain using Fourier transform to extract the predetermined frequency component. The predetermined frequency is desirably a frequency at which an amplitude value or power is maximized as a result of Fourier transform of the temporal waveform of light generated by the light source 103. For example, the frequency may be based on the pulse width of the light generated by the light source 103. An example of such a frequency is a frequency with a half cycle or a quarter cycle equal to the half width of a pulse, a frequency close thereto, or a harmonic frequency thereof. The present invention is not limited to these frequencies but any frequency may be used provided that the frequency ensures a sufficient SN ratio. Furthermore, the background optical coefficient is calculated using an inverse problem calculation for a phase modulation measurement method. The method will be described below in detail. The result of the calculation is output to the light intensity acquiring unit 110.

<<Light Intensity Acquiring Unit 110>>

The light intensity acquiring unit 110 is a unit that calculates the distribution of the intensity of light (the distribution of light intensity) in the region of interest 102 during photoacoustic measurement using the calculated background optical coefficient. The intensity of light can be calculated using, for example, a method of solving an equation describing the behavior of optical energy (for example, a diffusion equation or a transport equation) in accordance with a finite element method, a difference method, or the like, or a Monte Carlo method of executing calculations by considering the behavior of optical energy to be the statistical behavior of photons. The method will be described below in detail. The calculated distribution of light intensity is output to the information acquiring unit 111.

<<Information Acquiring Unit 111>>

The information acquiring unit 111 is a unit that acquires the distribution of the absorption coefficient in the region of interest 102 based on the distribution of initial sound pressure and the distribution of light intensity in the region of interest 102. This method will be described below in detail.

A workstation may typically be used for the reconstruction unit 108, the frequency analysis unit 109, the light intensity acquiring unit 110, and the information acquiring unit 111. However, these units may be implemented using hardware designed in a dedicated manner. When a computer such as a workstation is used, the process of each of the above-described units is executed by pre-programmed software.

<<Display Unit 112>>

The display unit 112 is a unit that presents the distribution of the absorption coefficient to a measurer. For example, the absorption coefficient may be displayed directly as a numerical value or in the form of a two-dimensional image or a volume rendering image. Moreover, the composition ratio or concentration of the tissue may be calculated based on the absorption coefficient and displayed. For example, oxygen saturation may be displayed.

<<Object 101>>

The object 101 does not provide the present invention but will be described below.

The object 101 is an object of measurement. The object 101 is typically a living body but may be a phantom that simulates the acoustic and optical characteristics of the living body. The photoacoustic measurement apparatus can image a light absorber with a large absorption coefficient which is present inside the object 101. When the object is a living body, the target of imaging is hemoglobin, water, melanin, collagen, lipid, or the like.

<Method for Calculating the Absorption Coefficient>

Now, a method for determining the absorption coefficient of the region of interest will be described. The absorption coefficient with respect to the inside of the object can be expressed using Formula 1. The initial sound pressure of an acoustic wave generated in the object is denoted by $P_0$. A Grueneisen constant is denoted by $\Gamma$. Furthermore, the intensity of light reaching the region of interest in the object is denoted by $\phi$. The absorption coefficient is denoted by $\mu_{a\_i}$.

The Gruenisen constant is obtained by dividing the product of the coefficient of volumetric expansion of the object and the square of the velocity of sound by constant pressure specific heat. As described above, the Gruenisen constant may be considered to be a constant value when the object is a living body. That is, the target distribution of the absorption coefficient can be obtained when the distribution of initial sound pressure and the distribution of light intensity in the region of interest can be acquired.

[Math 1]

$$P_0 = \Gamma \cdot \mu_{a\_i} \cdot \Phi \quad \text{Formula 1}$$

Now, a method for acquiring the distribution of light intensity in the region of interest will be described. The distribution of light intensity in the region of interest can be expressed using a diffusion equation that is independent of time, for example, Formula 2.

In Formula 2, a position vector representing a position in the object is denoted by r, and the light intensity at r is denoted by $\phi(r)$. Furthermore, the background scattering coefficient of the object is denoted by $\mu_s'\_b(r)$, and the background absorption coefficient of the object is denoted by $\mu_{a\_b}(r)$. A light source term is denoted by q(r). The background scattering coefficient and background absorption coefficient of the object need to be determined in order to obtain the intensity of light reaching the region of interest. Formula 2 is described using the sum of the first term including only $\mu_s'\_b$, the second term including only $\mu_{a\_b}$, and the third term including neither $\mu_s'\_b$ nor $\mu_{a\_b}$. Thus, to solve Formula 2, the background scattering coefficient $\mu_s'\_b$ and the background absorption coefficient $\mu_{a\_b}$ each need to be acquired.

[Math 2]

$$\nabla \cdot \left[ \frac{1}{3\mu_{s\_b}'(r)} \nabla \phi(r) \right] - \mu_{a\_b}(r) \cdot \phi(r) + q(r) = 0 \quad \text{Formula 2}$$

<<Summary of the Time Resolved Measurement Method and the Phase Modulation Measurement Method>>

In order to acquire each of the two background optical coefficients, it is necessary to measure the intensity of light transmitted through the object and to estimate the background optical coefficient using the time resolved measurement method or the phase modulation measurement method.

First, the time resolved measurement method will be described. In the time resolved measurement method, the object is irradiated with light with a short pulse width of several hundred picoseconds or shorter, and light propagated through the object is detected to acquire the temporal waveform of the light intensity. Then, the following is fitted to the acquired temporal waveform using the background optical coefficients $\mu_{a\_b}$ and $\mu_s'\_b$: an analytical solution indicative of the light intensity in a light scattering object (an analytical solution for the diffusion equation or the like) or a numerically calculated temporal waveform (which is obtained using a diffusion equation numerical solution or the Monte Carlo method). Finally, the background optical coefficient obtained when both waveforms sufficiently match each other is determined to be the background optical coefficient of the object. This corresponds to a solution for the inverse problem.

Figure 5A:
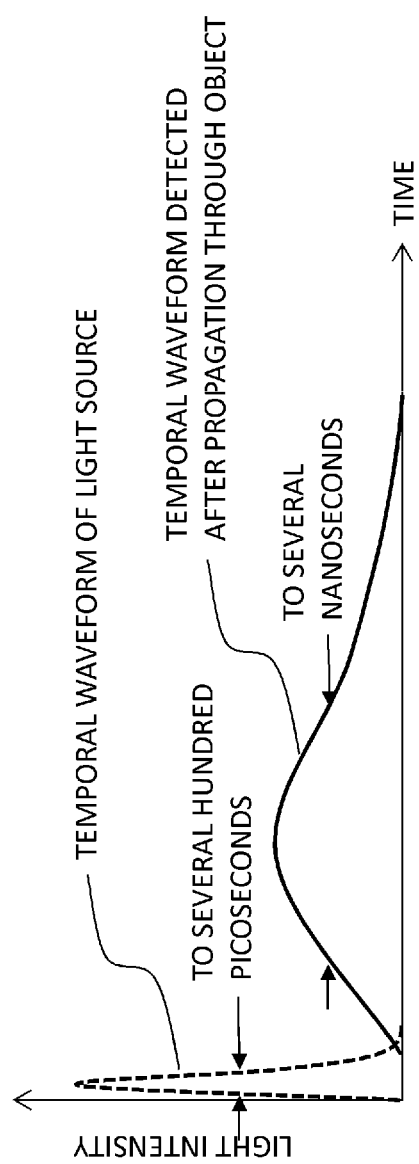
FIGS. 5A and 5B are diagrams showing a temporal waveform obtained using a time resolved measurement method.

FIG. 5A schematically shows a temporal waveform. Light propagated through the object has passed through various scattering paths and is thus observed as a temporally broadened waveform. For the background optical coefficient of a common living body, the extent of the temporal waveform is approximately several nanoseconds. When the pulse width of the light source is sufficiently short with respect to the extent, a rising portion of the detected temporal waveform in the initial stage principally has information on the background scattering coefficient $\mu_s'\_b$, and a latter relaxed portion of the temporal waveform principally has information on the background absorption coefficient $\mu_{a\_b}$.

Thus, when the time resolved measurement method is performed using a light source with a short pulse width of several hundred picoseconds, $\mu_{a\_b}$ and $\mu_s'\_b$ are uniquely determined from the measured temporal waveform. As a result, each of the two background optical coefficients can be accurately acquired.

If the irradiation light has a longer pulse width, the extent of the temporal waveform inherent in the background optical coefficient is included in the pulse width of the light source. For steady-state light with a infinite pulse width, the extent of the temporal waveform is completely lost, allowing only information on the light intensity to be obtained. Thus, with only one set of information (light intensity) being available relative to two variables—$\mu_{a\_b}$ and $\mu_s'\_b$—, a countless number of combinations of $\mu_{a\_b}$ and $\mu_s'\_b$ which satisfy the detected light intensity are present, making the determination of $\mu_{a\_b}$ and $\mu_s'\_b$ difficult.

Non-Patent Document 1 describes an embodiment in which the background optical coefficients of the normal breasts of 30 objects are measured using a light source with a pulse width of 140 picoseconds or shorter.

With reference to the embodiment described in Non-Patent Document 1, a detection time waveform for an ideal pulsed light source with a pulse width of zero was calculated using one of combinations of the 30 optical coefficients $\mu_{a\_b}$ and the 30 optical coefficients $\mu_s'\_b$ that leads to the shortest extent of the temporal waveform from the living body.

The background optical coefficients used in this case are the maximum value of $\mu_{a\_b}$, 0.0078 [/mm] and the minimum value of $\mu_s'\_b$, 0.63 [/mm]. Light detected later on the temporal waveform has been heavily scattered and thus has a large optical path length. Thus, the light has been more significantly absorbed and the intensity is reduced. The larger the background absorption coefficient is, the greater the decay of light in the later part of the temporal waveform compared to light in the early part of the temporal waveform would become. Thus, the extent of the temporal waveform decreases with the background absorption coefficient. Furthermore, the smaller the scattering coefficient is, the lower the probability that light travels through various scattering paths would become. Thus, the extent of the temporal waveform resulting from differences in optical path length decreases consistently with the scattering coefficient.

Figure 5B:
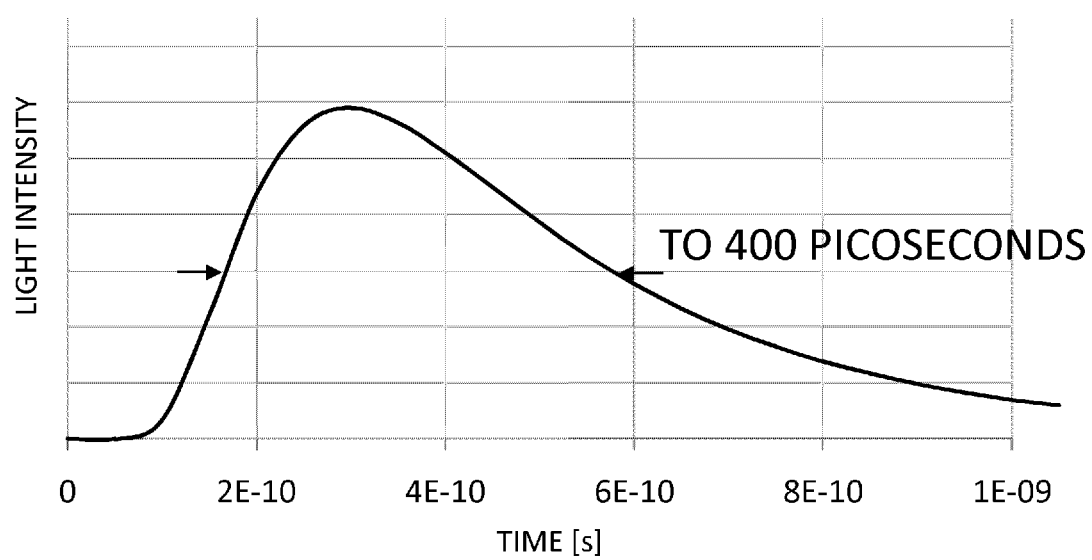

FIG. 5B shows the results of calculation of the extent of the temporal waveform using the background optical coefficients. The calculated extent of the temporal waveform is 400 picoseconds, indicating that the pulse width of the light source, 140 picoseconds, is shorter than the extent.

As described above, the time resolved measurement allows $\mu_{a\_b}$ and $\mu_s'\_b$ to be independently and accurately measured using a light source with a pulse width shorter than the extent of the temporal waveform from the object.

Now, the phase modulation measurement method will be described. The phase modulation measurement method is a method of irradiating the object with light modulated using a frequency of the order of megahertz to gigahertz (intensity modulated light) and measuring the amplitude decay and phase difference of the light propagated through the object. The amplitude decay refers to the ratio of the amplitude of detected light with respect to the amplitude of light generated by the light source. The phase difference refers to the lag of the phase of the detected light with respect to the phase of the light generated by the light source.

In the phase modulation measurement method, the amplitude decay and phase difference calculated using an analytical solution or a numerical calculation are optimized so as to become equal to the measured amplitude decay and phase difference, using $\mu_{a\_b}$ and $\mu_s'\_b$ as variables. Then, the background optical coefficients obtained when these values become equal are determined to be the background optical coefficients of the object. This method also corresponds to an inverse problem calculation as is the case with the time resolved measurement method.

Now, description will be given which relates to the effects of using a pulsed light source used for normal photoacoustic imaging instead of a short pulsed light source when measuring the background optical coefficient using the time resolved measurement method.

The pulse width of light used for photoacoustic imaging needs to satisfy a condition (stress confinement condition) for the efficient generation of an acoustic wave from a light absorber present in the region of interest. The stress confinement condition is expressed by Formula 3.

[Math 3]

$$t_{irradiation} \ll \tau_s, \tau_s = \frac{d_c}{v_s} \qquad \text{Formula 3}$$

In Formula 3, light irradiation time is denoted by $t_{irradiation}$, and stress relaxation time is denoted by $\tau_s$.

The size of the light absorber in the region of interest is denoted by $d_c$, and the velocity of sound in the object is denoted by $v_s$. Formula 3 indicates that, if the light irradiation time is sufficiently shorter than the stress relaxation time, the propagation of an elastic wave during irradiation can be neglected, allowing a photoacoustic wave to be generated. When size of the light absorber in the region of interest is 1 [mm] and the velocity of sound is 1,540 [m/s], $\tau_s$ is about 650 [ns]. A photoacoustic imaging apparatus needs to set the pulse width equal to or smaller than $\tau_s$, and thus, a light source is generally used which has a pulse width of several nanoseconds to several hundred nanoseconds.

The pulse width is much longer than the pulse width suitable for the time resolved measurement method.

The pulse width of light used for photoacoustic imaging is intermediate between the pulse width suitable for the time resolved measurement method (several hundred picoseconds or shorter) and the infinite pulse width of steady-state light. Thus, the measured temporal waveform and the calculated temporal waveform involve a plurality of combinations of $\mu_{a\_b}$ and $\mu_s'_{\_b}$, preventing the coefficients from being uniquely determined. This is also expected from the fact that the general time resolved measurement method allows a unique combination of $\mu_{a\_b}$ and $\mu_s'_{\_b}$ to be determined and that steady-state light involves a countless number of combinations of $\mu_{a\_b}$ and $\mu_s'_{\_b}$. That is, the use of pulsed light of nanosecond order for the time resolved measurement prevents the background optical coefficients from being determined, reducing the accuracy of measurement.

Figure 6:
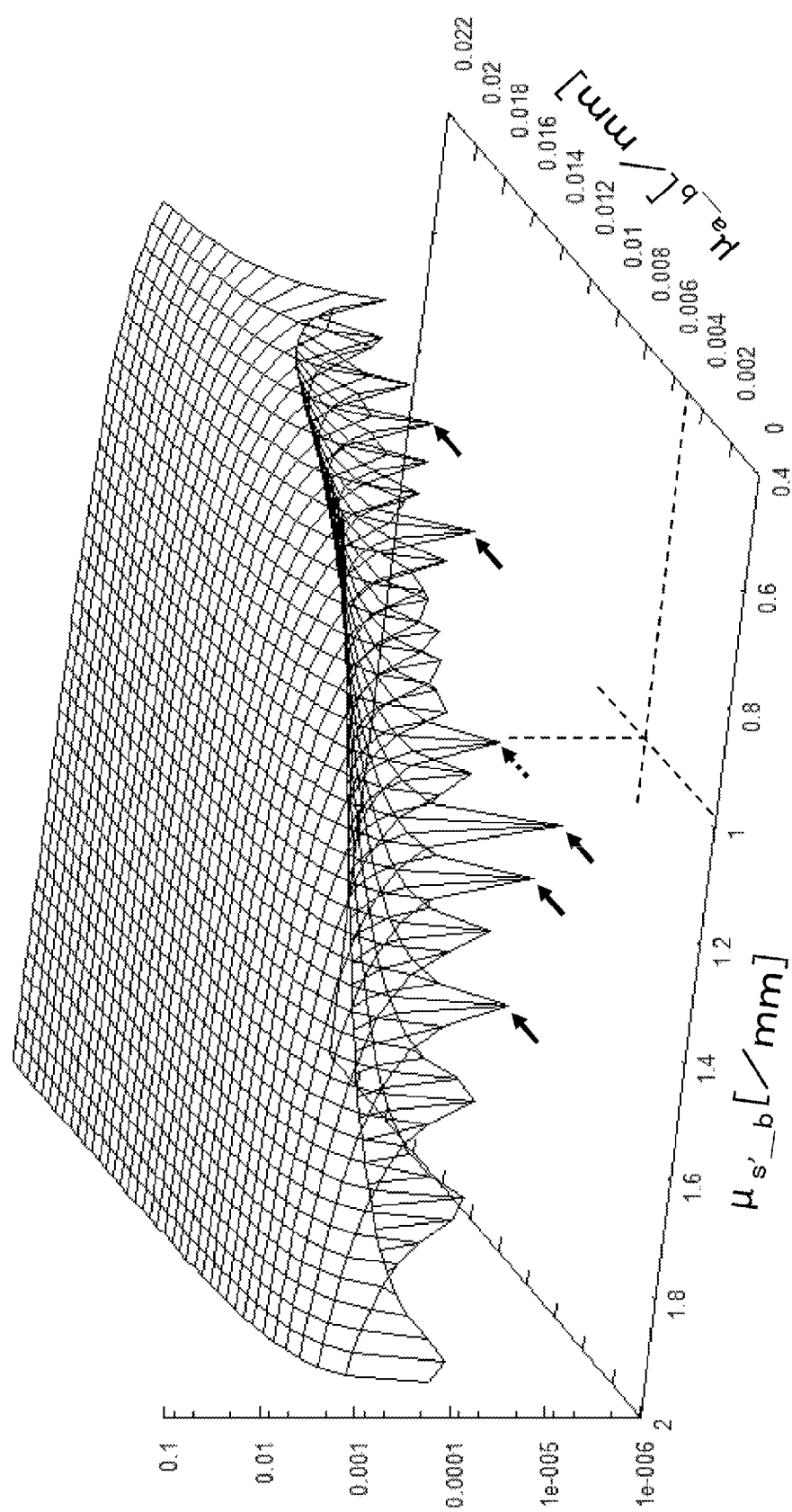
FIG. 6 is a diagram illustrating the results of calculation of a background optical coefficient according to the conventional technique.
Figure 7:
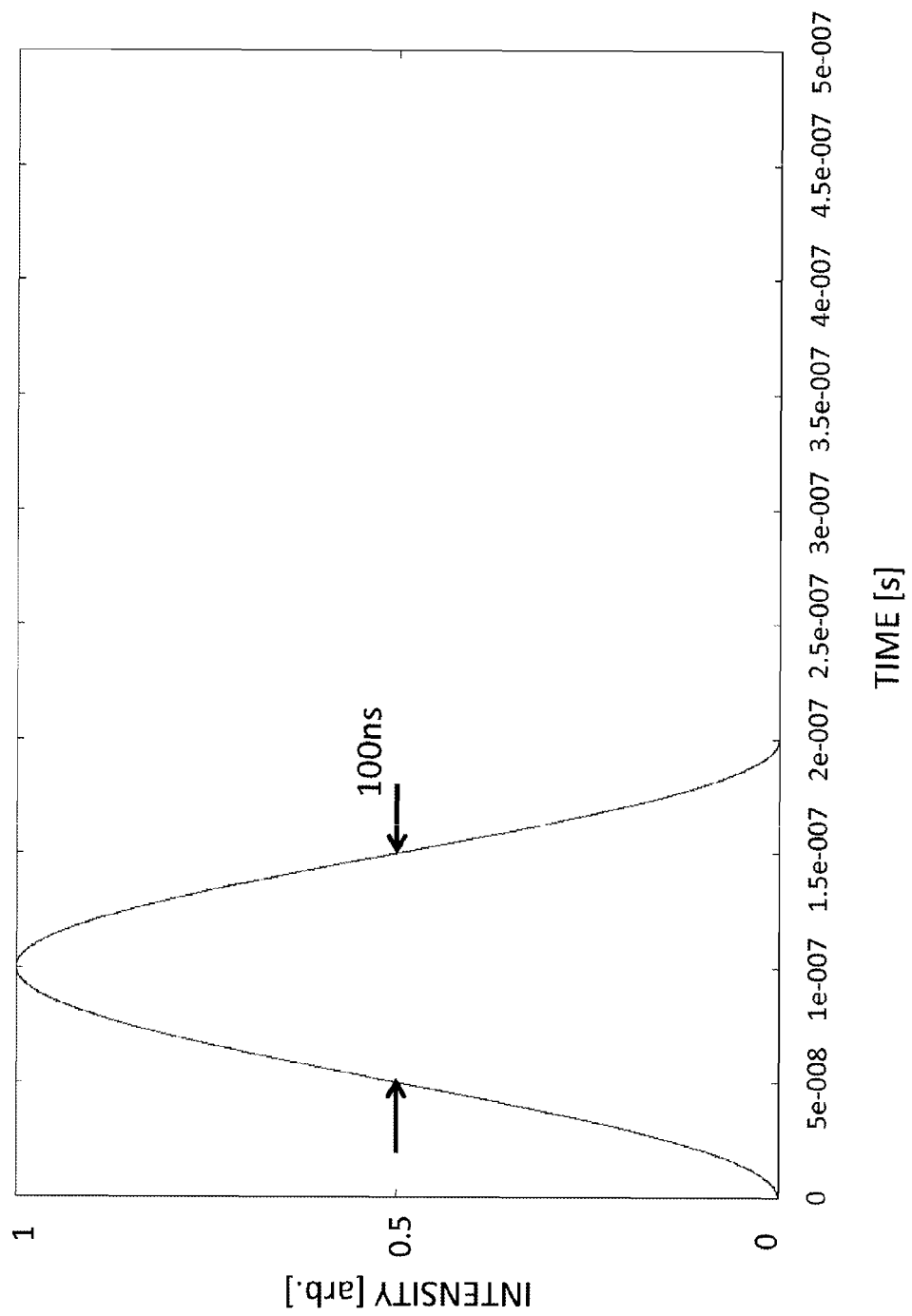
FIG. 7 is a diagram showing the temporal waveform of pulsed light generated by a light source.

FIG. 6 shows the mean square residual between a detected temporal waveform calculated by using the Monte Carlo method and setting $\mu_{a\_b}$ and $\mu_s'_{\_b}$ to 0.005 [/mm] and 0.995 [/mm], respectively, and a detected temporal waveform calculated by using an analytical solution for the diffusion equation and setting $\mu_{a\_b}$ and $\mu_s'_{\_b}$ to different values. The waveform of the light source is a waveform with a full width at half maximum of 100 nanoseconds as shown in FIG. 7.

In FIG. 6, two axes of abscissas indicate $\mu_{a\_b}$ and $\mu_s'_{\_b}$, respectively, and the axis of ordinate indicates the mean square residual. In FIG. 6, besides $\mu_{a\_b}$=0.005 [/mm] and $\mu_a'_{\_b}$=0.995 [/mm] as shown by dashed arrows, a plurality of minimum values of the residual as shown by solid arrows is present. This indicates that a plurality of combinations of $\mu_{a\_b}$ and $\mu_s'_{\_b}$ is present.

When an inverse problem calculation was worked out with a view to obtain the temporal waveform calculated using $\mu_{a\_b}$=0.005 [/mm] and $\mu_s'_{\_b}$=0.995, the calculation resulted in $\mu_{a\_b}$=0.011 [/mm] and $\mu_s'_{\_b}$=0.639 [/mm], which correspond to significant errors. The inverse problem calculation uses a method of globally searching the entire area in FIG. 6 and is thus prevented from resulting in a local solution.

As described above, when the background optical coefficients of the object are measured using the light source used for photoacoustic imaging, a combination of $\mu_{a\_b}$ and $\mu_s'_{\_b}$ may be selected which is different from the actual background optical coefficients, resulting in a reduction in the accuracy of the measurement.

The photoacoustic imaging apparatus generally uses a light source with a pulse width of several nanoseconds to several hundred nanoseconds which satisfies the stress confinement condition. However, for the time resolved measurement, a light source needs to be used which has a pulse width of picoseconds order. Thus, a light source for the time resolved measurement needs to be separately provided, leading to increased costs.

In contrast, the present invention proposes a method of allowing the background optical coefficients to be measured using the light source commonly used for photoacoustic imaging.

<<Method for Measuring the Background Optical Coefficients>>

A specific method for measuring the background optical coefficients will be described.

The amplitude decay and phase difference resulting from Fourier transform of a temporal waveform in the time resolved measurement method are equal to the amplitude decay and phase difference in the time resolved measurement method. That is, the phase modulation measurement method and the time resolved measurement method are in an equivalent relation. Thus, with the amplitude decay and phase difference measured using the phase modulation measurement method, $\mu_{a\_b}$ and $\mu_s'_{\_b}$ can be uniquely determined as is the case with the time resolved measurement method (equivalently to the time resolved measurement method).

Light generated by the light source 103 is light with a pulse width of several nanoseconds to several hundred nanoseconds. The reciprocal of the pulse width is several megahertz to several hundred megahertz. That is, pulsed light generated by the light source 103 has a frequency component of megahertz order. To acquire the frequency component, it is possible to convert an optical signal into the frequency domain and to acquire the corresponding frequency component. Thus, when the acquired optical signal is converted into a frequency component, the phase modulation measurement method can be implemented without changing the pulse width of irradiation light. For example, the pulse width of irradiation light may be set within the range of 10 nanoseconds to 650 nanoseconds, which is commonly used for photoacoustic imaging and which is unsuitable for the time resolved measurement method. Moreover, the pulse width of irradiation light may be set within the range of 100 nanoseconds to 650 nanoseconds.

Specifically, the frequency analysis unit 109 acquires the amplitude decay and phase difference of the obtained frequency component, and executes an inverse problem calculation for the phase modulation measurement to independently acquire $\mu_{a\_b}$ and $\mu_{s}'_{\_b}$. Since the time resolved measurement is equivalent to the phase modulation measurement method, the acquired $\mu_{a\_b}$ and $\mu_{s}'_{\_b}$ have unique values.

The frequency for which the frequency component is acquired is a frequency at which an amplitude value or power is maximized as a result of Fourier transform of the temporal waveform of light generated by the light source 103. For example, it is possible to use a frequency with a half cycle equal to the half width of the pulsed light (1/((half pulse width)[s]×2)[Hz]) or a frequency with a quarter cycle equal to the half width of the pulsed light (1/((half pulse width)[s]×4)[Hz]). The present invention is not limited to these frequencies but any frequency may be used provided that the frequency ensures a sufficient SN ratio. Furthermore, the accuracy of the calculation may be increased by determining the components of a plurality of other frequencies.

<<Processing Flowchart>>

Figure 8:
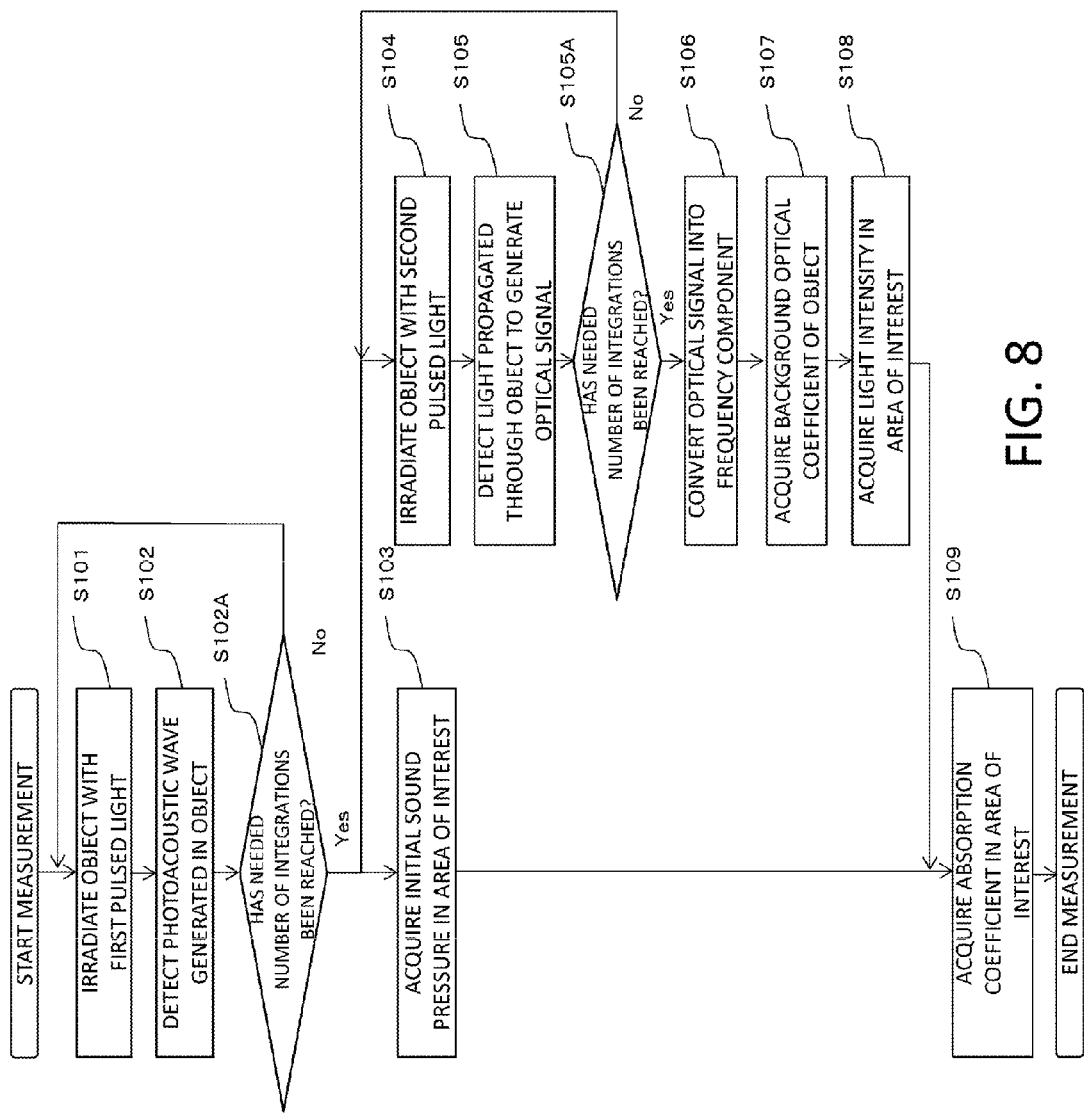
FIG. 8 is a diagram showing the flow of a process executed by the object information acquiring apparatus according to the first embodiment.

Now, a processing method executed by an object information acquiring apparatus according to the first embodiment will be described with reference to FIG. 8.

Step S101 is a step of irradiating the object with pulsed light used for photoacoustic measurement. The pulsed light used for photoacoustic imaging is hereinafter referred to as the first pulsed light.

In step S101, first, the measurement unit 105 is moved to a position suitable for measurement of the region of interest 102. The optical systems are set so that the pulsed light is provided to the object 101 over a large irradiation area. Furthermore, the irradiation interval of the pulsed light is set to a time suitable for reception of photoacoustic waves. These settings are desirably automatically performed by the apparatus but may be carried out by the measurer.

Then, the light source 103 generates and provides pulsed light to the object 101 via the measurement unit 105.

Step S102 is a step of receiving a photoacoustic wave generated in the object.

In step S102, the acoustic wave probe 106 receives the photoacoustic wave generated in the region of interest 102 as a result of irradiation with the first pulsed light and converts the photoacoustic wave into an acoustic wave signal. In this case, photoacoustic waves are repeatedly received to integrate signals together until the signals exhibit a sufficient SN ratio value (step S102A).

Step S103 is a step of acquiring the distribution of initial sound pressure in the region of interest.

In step S103, the reconstruction unit 108 reconstructs the signal acquired in step S102 to acquire the distribution of initial sound pressure in the region of interest 102.

Step S104 is a step of irradiating the object with pulsed light used for measurement of the background optical coefficients. The pulsed light used for measurement of the background optical coefficients is hereinafter referred to as the second pulsed light.

In step S104, the optical systems are set so that the pulsed light is provided to the object 101 over a small irradiation area. Furthermore, the irradiation interval of the pulsed light is set to a time suitable for detection of propagated light. These settings are desirably automatically performed by the apparatus but may be carried out by the measurer.

Then, the light source 103 generates and provides pulsed light to the object 101 via the measurement unit 105.

Step S105 is a step of detecting the pulsed light used for measurement of the background optical coefficients.

In step S105, the photodetector 107 detects the pulsed light provided to the object 101 and propagated through the object 101, to generate an optical signal indicative of the transition of the intensity of the detected light. In this case, the pulsed light is repeatedly detected to integrate optical signals together until the optical signals exhibit a sufficient SN ratio value (step S105A).

Step S106 is a step of converting the generated optical signal into a predetermined frequency component.

In step S106, the frequency analysis unit 109 converts the optical signal into the frequency domain and acquires the predetermined frequency component. Then, the amplitude decay is acquired using the amplitude of the acquired frequency component and the amplitude of the frequency component of pre-acquired pulsed light. Furthermore, the phase difference is acquired using the phase of the acquired frequency component and the phase of the frequency component of the pulsed light.

Step S107 is a step of calculating the background optical coefficients of the object.

In step S107, the frequency analysis unit 109 calculates the background optical coefficients of the object 101 in accordance with the phase modulation measurement method using the amplitude decay and phase difference acquired in step S106.

Step S108 is a step of acquiring the distribution of light intensity in the region of interest.

In this step, the light intensity acquiring unit 110 acquires the distribution of light intensity in the region of interest 102 in use of the background optical coefficient obtained in step S107.

Step S109 is a step of acquiring the distribution of absorption coefficient in the region of interest.

In step S109, the information acquiring unit 111 acquires the distribution of the absorption coefficient in the region of interest using the distribution of initial sound pressure acquired in step S103 and the distribution of light intensity acquired in step S109. The acquired distribution of the absorption coefficient is presented to the measurer through the display unit 112.

Step S103 is desirably executed in parallel with steps S104 to S108. Since steps S104 to S108 are executed while the image reconstruction process (step S103), which is time-consuming, is being carried out, this parallel processing enables a reduction in the overall measurement time compared to sequential processing.

Example 1

The effects of the present invention will be described with reference to FIG. 9. First, a waveform from the light source 103 as shown in FIG. 7 was converted into the frequency domain, and with the half cycle considered to be 100 [ns], which is equal to the half width of the pulsed light, the amplitude and phase of a frequency component of 1/(100 [ns]×2)=5 [MHz] were acquired. Then, an object with background optical coefficients $\mu_{a\_b}$ and $\mu_{s}'_{\_b}$ of 0.005 [/mm] and 0.995 [/mm], respectively, was prepared, and an optical signal detected as a result of incidence of light with the waveform shown in FIG. 7 was acquired. The optical signal was converted into the frequency domain, and the amplitude and phase of the 5-[MHz] component were calculated.

The ratio of the amplitude of the optical signal to the amplitude of the light source was determined as amplitude decay. The lag of the phase of the optical signal with respect to the light source was determined as a phase difference. These calculations were performed with the values of $\mu_{a\_b}$ and $\mu_{s}'_{\_b}$ changed to calculate the mean square residual for the amplitude decay and the phase difference at $\mu_{a\_b}$=0.005

[/mm] and $\mu_{s\_b}'$=0.995 [/mm]. In FIG. 9, two axes of abscissas indicate $\mu_{a\_b}$ and $\mu_{s\_b}'$, respectively, and the axis of ordinate indicates the mean square residual.

Figure 9:
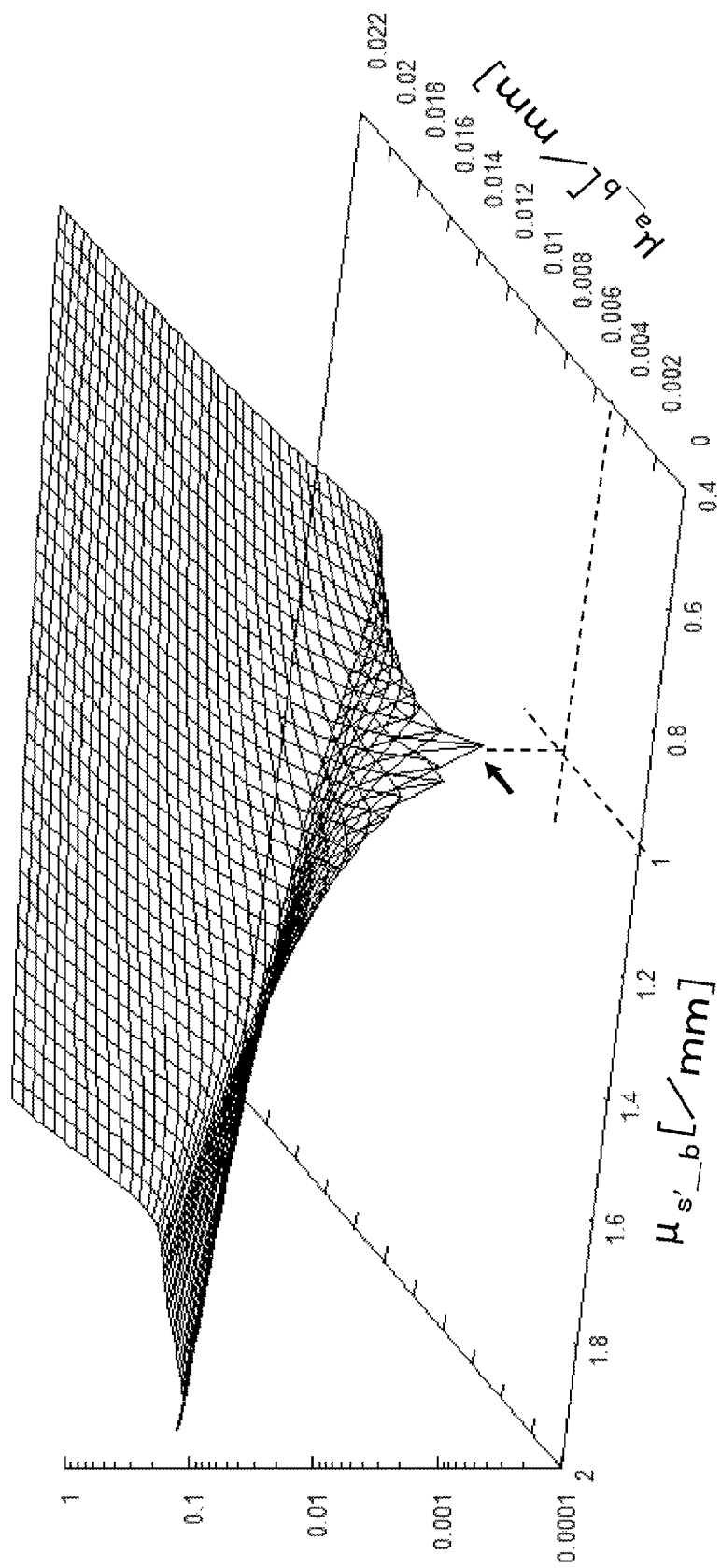
FIG. 9 is a diagram illustrating the results of calculation of the background optical coefficient.

FIG. 9 indicates that the mean square residual exhibits the only minimum value at a point with $\mu_{a\_b}$=0.005 [/mm] and $\mu_{s\_b}'$=0.995 [/mm]. When an inverse problem calculation was performed with a view to obtain the amplitude decay and the phase difference at $\mu_{a\_b}$=0.005 [/mm] and $\mu_{s\_b}'$=0.995 [/mm], the calculation resulted in $\mu_{a\_b}$=0.0051 [/mm] and $\mu_{s\_b}'$=0.980 [/mm], which are close to the actual values.

As described above, if the time resolved measurement method is performed using the pulsed light, without any modification, generated by the light source 103, the solution for the inverse problem fails to be uniquely determined as shown in FIG. 6. In contrast, the photoacoustic measurement apparatus according to the first embodiment has been demonstrated to allow the solution for the inverse problem to be uniquely determined, enabling the background optical coefficients of the object to be accurately determined.

The first embodiment treats the background optical coefficients for the inside of the object as uniform values. When the background optical coefficients have uniform values, $\mu_{s\_b}'(r)$ and $\mu_{a\_b}(r)$ in Formula 2 can be described as constants that are independent of the position r, allowing Formula 2 to described like Formula 4. For example, for an object such as the breast or the like, the entire area except for a tumor, which is a light absorber, has a substantially homogeneous composition, and the tumor is sufficiently small compared to the whole object. Thus, the optical characteristics of the whole object may be considered to be uniform without any problem.

Furthermore, since the pulse width of the light source 103 is sufficiently larger than the above-described extent of the temporal waveform, the diffusion equation allows the pulsed light to be treated as continuous wave (CW) light. This enables the use of the diffusion equation, which is independent of time.

[Math 4]

$$\frac{1}{3\mu_{s\_b}'} \nabla \cdot [\nabla \phi(r)] - \mu_{a\_b} \cdot \phi(r) + q(r) = 0 \quad \text{Formula 4}$$

Second Embodiment

In the first embodiment, the optical systems in the measurement unit are individually switched to each other to change the irradiation area of pulsed light for the object. In contrast, a second embodiment is an embodiment in which a plurality of measurement units is provided to allow photoacoustic measurement and measurement of the background optical coefficients to be performed in parallel.

Figure 10:
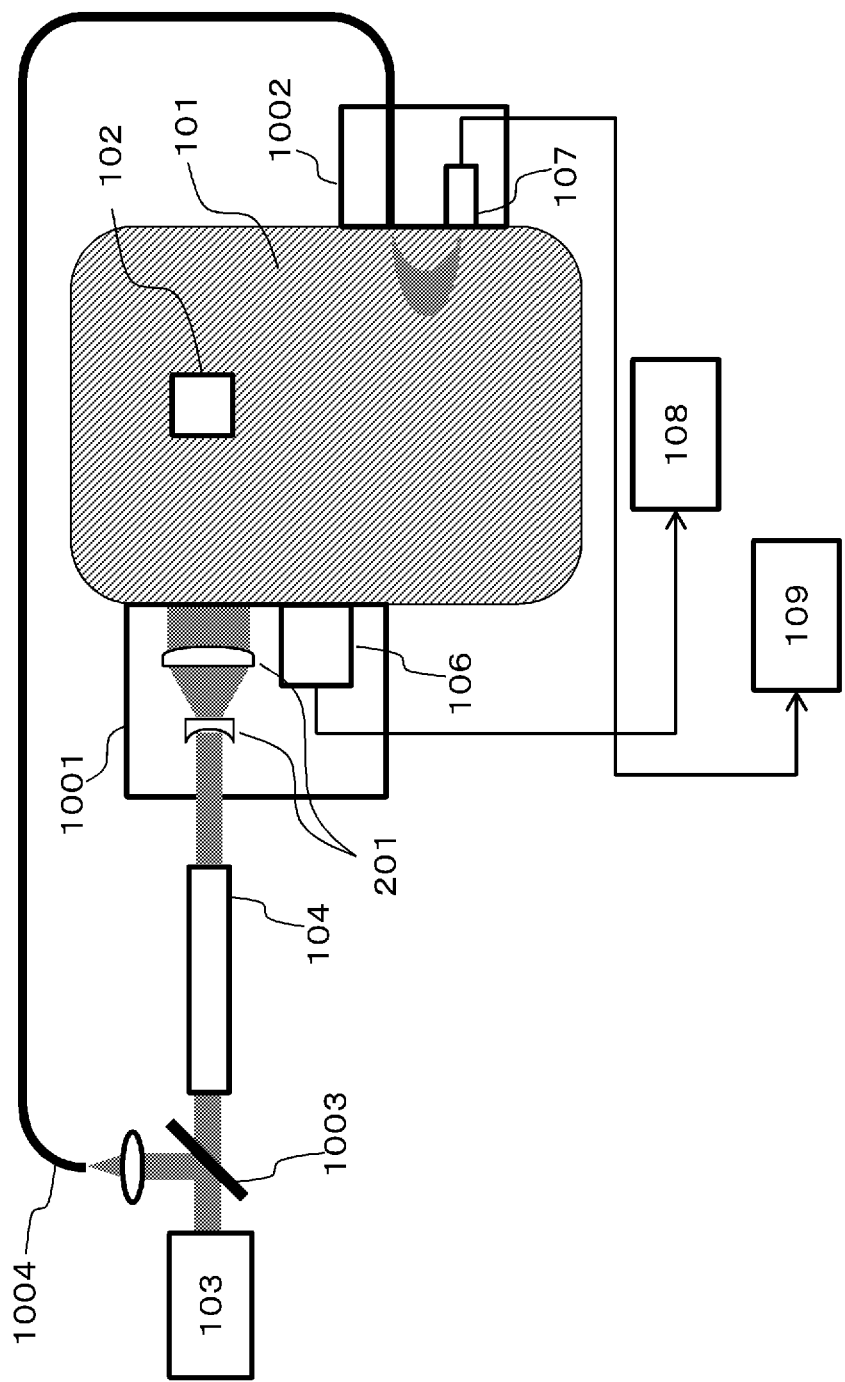
FIG. 10 is a diagram showing a configuration of an object information acquiring apparatus according to a second embodiment.

With reference to FIG. 10, an apparatus configuration of a photoacoustic measurement apparatus according to the second embodiment will be described. Components of the second embodiment which are the same as the corresponding components of the first embodiment are denoted by the same reference numerals and will not be described below. Furthermore, components not directly related to the description of the embodiment are not illustrated.

The second embodiment includes a first measurement unit 1001 used for photoacoustic measurement and a second measurement unit 1002 used for measurement of the background optical coefficients. The measurement units are independent of each other and are positioned so as to prevent irradiation light from one of the measurement units from affecting measurement performed by the other measurement unit. For example, the measurement units are arranged on opposite surfaces across the object as shown in FIG. 10.

This arrangement allows pulsed light provided by one of the measurement units to reach the other measurement unit after being significantly decayed by absorption and scattering of light inside the object. This enables a reduction in the adverse effect of the pulsed light on the measurement performed by the other measurement unit.

The photoacoustic measurement apparatus according to the second embodiment has, similarly to the first embodiment, a light source 103, a light guiding unit 104, an acoustic wave probe 106, a photodetector 107, a reconstruction unit 108, a frequency analysis unit 109, a light intensity acquiring unit 110, an information acquiring unit 111, and a display unit 112. Furthermore, the photoacoustic measurement apparatus according to the second embodiment has the first measurement unit 1001, the second measurement unit 1002, a beam splitter 1003, and a second light guiding unit 1004 as components specific to the second embodiment.

The beam splitter 1003 is a unit that splits pulsed light generated by the light source 103 into two paths. Beams resulting from the splitting of the pulsed light enter the light guiding unit 104 and the second light guiding unit 1004, respectively. The beam splitter may be, for example, a dielectric film splitter or a polarizing splitter which splits light into a transmitted beam and a reflected beam or a prism that divides a beam spot shape.

The second light guiding unit 1004 is a unit that guides a portion of the pulsed light resulting from the splitting performed by the beam splitter 1003, to the measurement unit 1001. Like the light guiding unit 104, the second light guiding unit 1004 may be an optical member such as a mirror or a prism, optical fibers, or the like. When optical fibers are used as the second light guiding unit 1004, a coupling optical system may be located between the beam splitter 1003 and the second light guiding unit 1004 in order to efficiently transmit light.

The first measurement unit 1001 is a unit that irradiates the object 101 with pulsed light emitted by the light guiding unit 104 and receiving a photoacoustic wave. The first measurement unit 1001 incorporates a beam expander 201 and provides pulsed light to the object over a large area.

Furthermore, the second measurement unit 1002 is a unit that irradiates the object 101 with pulsed light emitted by the second light guiding unit 1004 and that detects light propagated through the object. Pulsed light transmitted via the second measurement unit 1002 is provided to the object within a small area. For example, when the second light guiding unit 1004 is optical fibers, the exit end of the optical fibers may be in contact with the object. Additionally, an appropriate optical system may be provided between the second light guiding unit 1004 and the object 101.

Figure 11:
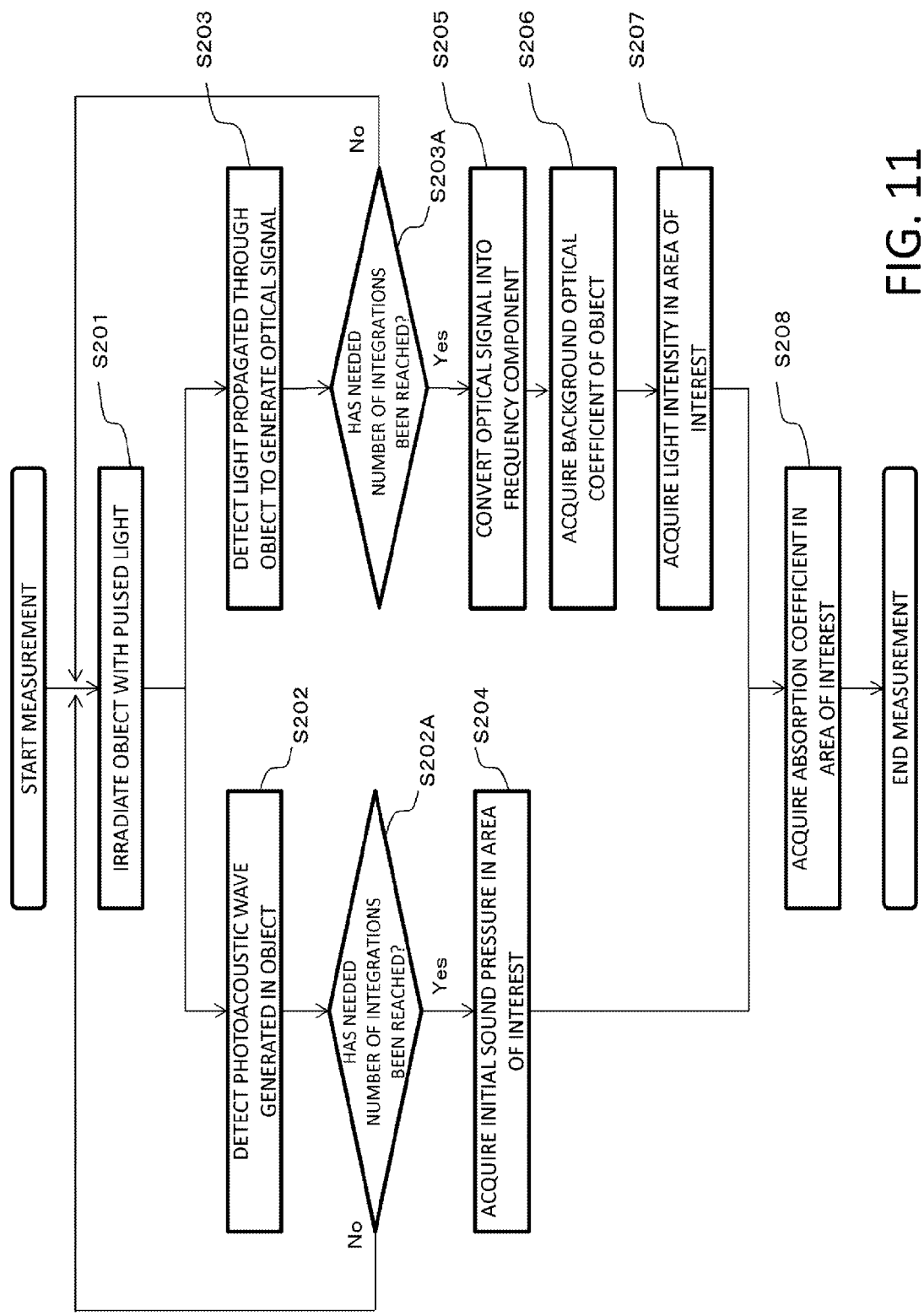
FIG. 11 is a diagram showing the flow of a process executed by the object information acquiring apparatus according to the second embodiment.

Now, with reference to FIG. 11, the flow of a process executed by an object information acquiring apparatus according to the second embodiment will be described. Steps S204, S205, S206, S207, and S208 in FIG. 11 are identical to steps S103, S106, S107, S108, and S109 according to the first embodiment and will thus not be described below.

Step S201 is a step of irradiating the object with pulsed light (first pulsed light) used for photoacoustic measurement.

In step S201, first, the first measurement unit 1001 is moved to a position suitable for measurement of the region of interest 102. The second measurement unit 1002 is placed at a position where pulsed light provided by the first measurement unit 1001 sufficiently decays. Preferably, the photodetector incorporated in the second measurement unit 1002 may be placed 7 cm or more away in direct distance from a position irradiated with light from the first measurement unit 1001.

Then, the emission interval of pulsed light generated by the light source 103 is set to the longer of either a time suitable for reception of a photoacoustic wave or a time suitable for detection of propagated light. This setting is desirably automatically performed by the apparatus but may be carried out by the measurer. Then, the light source 103 generates and provides pulsed light to the object 101 via each of the measurement units.

Step S202 is a step of receiving photoacoustic wave generated in the object.

In step S202, the acoustic wave probe 106 receives and converts the photoacoustic wave generated in the region of interest 102 as a result of irradiation with the first pulsed light, into a photoacoustic wave signal. In this case, photoacoustic waves are repeatedly received to integrate signals together until the signals exhibit a sufficient SN ratio value (step S202A).

Step S203 is a step of detecting pulsed light used for measurement of the background optical coefficients.

In step S203, the photodetector 107 detects the pulsed light provided to the object 101 and propagated through the object 101, to generate an optical signal indicative of the transition of the intensity of the detected light. In this case, the pulsed light is repeatedly detected to integrate optical signals together until the optical signal exhibits a sufficient SN ratio value (step S203A).

Steps S202 and S203 are synchronously executed. However, one of the steps that has reached the needed number of integrations first may proceed to the next step even while the other step is being executed.

Steps other than the described steps are similar to the corresponding steps according to the first embodiment.

The second embodiment allows photoacoustic measurement and measurement of the background optical coefficients to be simultaneously performed as described above. This enables a reduction in the time needed for the measurement.

Third Embodiment

According to the first and second embodiments, each of the background optical coefficients of the object is considered to be substantially uniform, and thus, a single value is calculated for the background optical coefficient. In contrast, according to a third embodiment, the background optical coefficient is measured at a plurality of positions on the object to generate a distribution of the background optical coefficient.

Figure 12A:
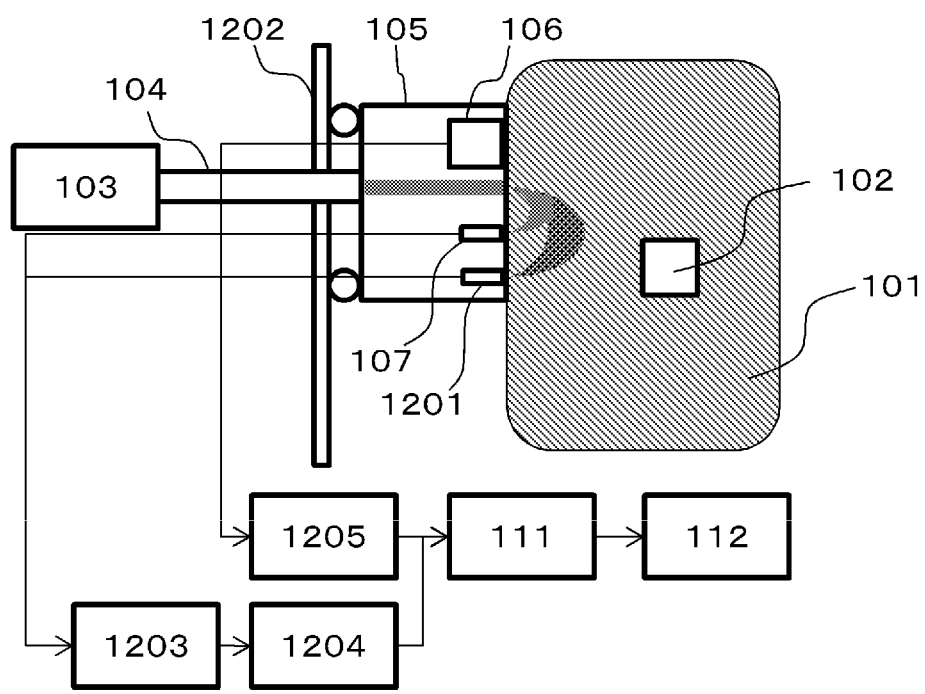
FIGS. 12A to 12C are diagrams showing a configuration of an object information acquiring apparatus according to a third embodiment.
Figure 12B:
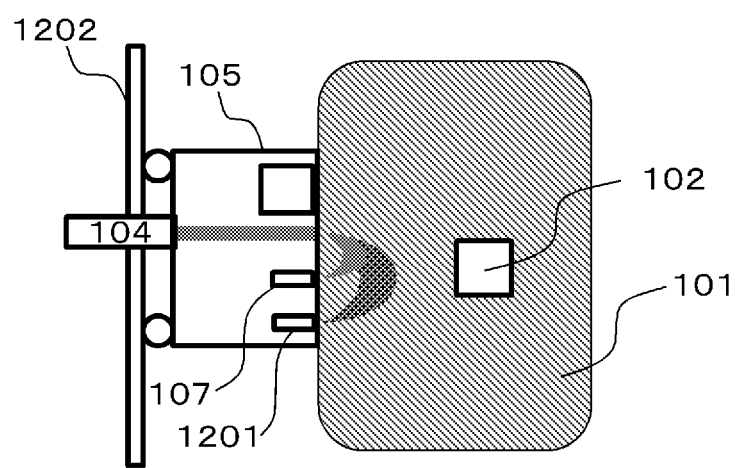
Figure 12C:
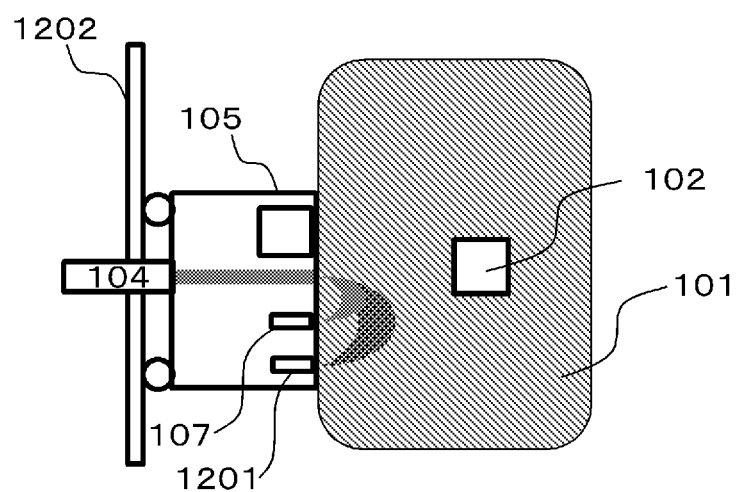

With reference to FIGS. 12A to 12C, an apparatus configuration of a photoacoustic measurement apparatus according to the third embodiment will be described. Components of the third embodiment which are the same as the corresponding components of the first embodiment are denoted by the same reference numerals and will not be described below. Furthermore, components not directly related to the description of the embodiment are not illustrated.

According to the third embodiment, pulsed light is detected at a plurality of positions on the object, a spatial distribution of each background optical coefficient (the distribution of each background optical coefficient) is calculated using the plurality of optical signals acquired. The distribution of the absorption coefficient in the region of interest can be more accurately determined by using the distribution of each background optical coefficient to calculate the distribution of light intensity.

As is the case with the first embodiment, the photoacoustic measurement apparatus according to the third embodiment incorporates a light source 103, a light guiding unit 104, a measurement unit 105, an information acquiring unit 111, and a display unit 112. Moreover, the measurement unit 105 is incorporated with the acoustic wave probe 106 and the photodetector 107.

Furthermore, the photoacoustic measurement apparatus according to the third embodiment has a moving unit 1202, a photodetector 1201, a frequency analysis unit 1203, a light intensity acquiring unit 1204, and a reconstruction unit 1205 as components specific to the third embodiment.

The photodetector 1201 has the same functions as those of the photodetector 107 but is installed at a position different from the position where the photodetector 107 is installed. The photodetector 1201 can thus detect light having traveled through a scattering path different from the scattering path of light detected by the photodetector 107.

The moving unit 1202 is a unit that moves the measurement unit 105. FIGS. 12A to 12C showcases where the moving unit 1202 has moved the measurement unit 105 to three different positions.

The reconstruction unit 1205 is different from the reconstruction unit according to the first embodiment in that the reconstruction unit 1205 executes an image reconstruction process based on a plurality of acoustic waves received at different positions. Examples of a reconstruction process of synthesizing signals received at a plurality of positions into one image include a method for back projection in the time domain, a reconstruction method based on time reversal, a method for reconstruction in the Fourier domain, and a model-based reconstruction method. The generated distribution of initial sound pressure is output to the information acquiring unit 111.

The frequency analysis unit 1203 is a unit that converts a plurality of optical signals acquired by the photodetector 107 and the photodetector 1201 into respective predetermined frequency components and that calculates the amplitude decay and phase difference for each of the positions. The frequency analysis unit 1203 then calculates the distribution of the background absorption coefficient $\mu_{a\_b}(r)$ and the distribution of the background scattering coefficient $\mu_{s}'_{\_b}(r)$. The distribution of each background optical coefficient is calculated using a diffusion equation for the frequency domain shown in Formula 5.

[Math 5]

$$\nabla \cdot \left[\frac{1}{3\mu'_{s\_b}(r)}\nabla \Phi(r)\right] - \left(\mu_{a\_b}(r) - \frac{i\omega}{v}\right)\Phi(r) + S(r) = 0 \quad \text{Formula 5}$$

In Formula 5, angular frequency [rad] is denoted by $\omega$, and a light source item with its intensity modulated based on the angular frequency $\omega$. Furthermore, $\phi(r)=A(r)\exp(ik|r|)$, the amplitude of the light intensity at a position r is denoted by A(r), and the phase difference at the position r is denoted by exp(ik|r|) (the wave number of light with its intensity modulated propagating through the object 101 is denoted by k)

First, the light irradiation position in FIG. 12A is set for S(r), and the A(r) and exp(ik|r|) of each of the photodetectors 107 and 120 are calculated. Similar calculations are executed on the positions in FIGS. 12B and 12C. The distribution of the background absorption coefficient $\mu_{a\_b}(r)$ and the distribution of the background scattering coefficient $\mu_s'\_{\_b}(r)$ are optimized so that, for all the amplitude decays and phase differences, the calculate value matches the measured value.

The distribution of the background absorption coefficient $\mu_{a\_b}(r)$ and the distribution of the background scattering coefficient $\mu_s'\_{\_b}(r)$ both resulting from the above-described calculations correspond to the distributions of the background optical coefficients of the object 101.

The light intensity acquiring unit 1204 is a unit that acquires the distribution of light intensity in the region of interest 102 using the distribution of each background optical coefficient acquired by the frequency analysis unit 1203. The intensity of light can be calculated using a method similar to the method according to the first embodiment. For example, when the diffusion equation is used, the equation may be solved by substituting the distributions of the background optical coefficients determined by the frequency analysis unit 1203 into the $\mu_{a\_b}(r)$ and $\mu_s'\_{\_b}(r)$ in Formula 2.

Figure 13:
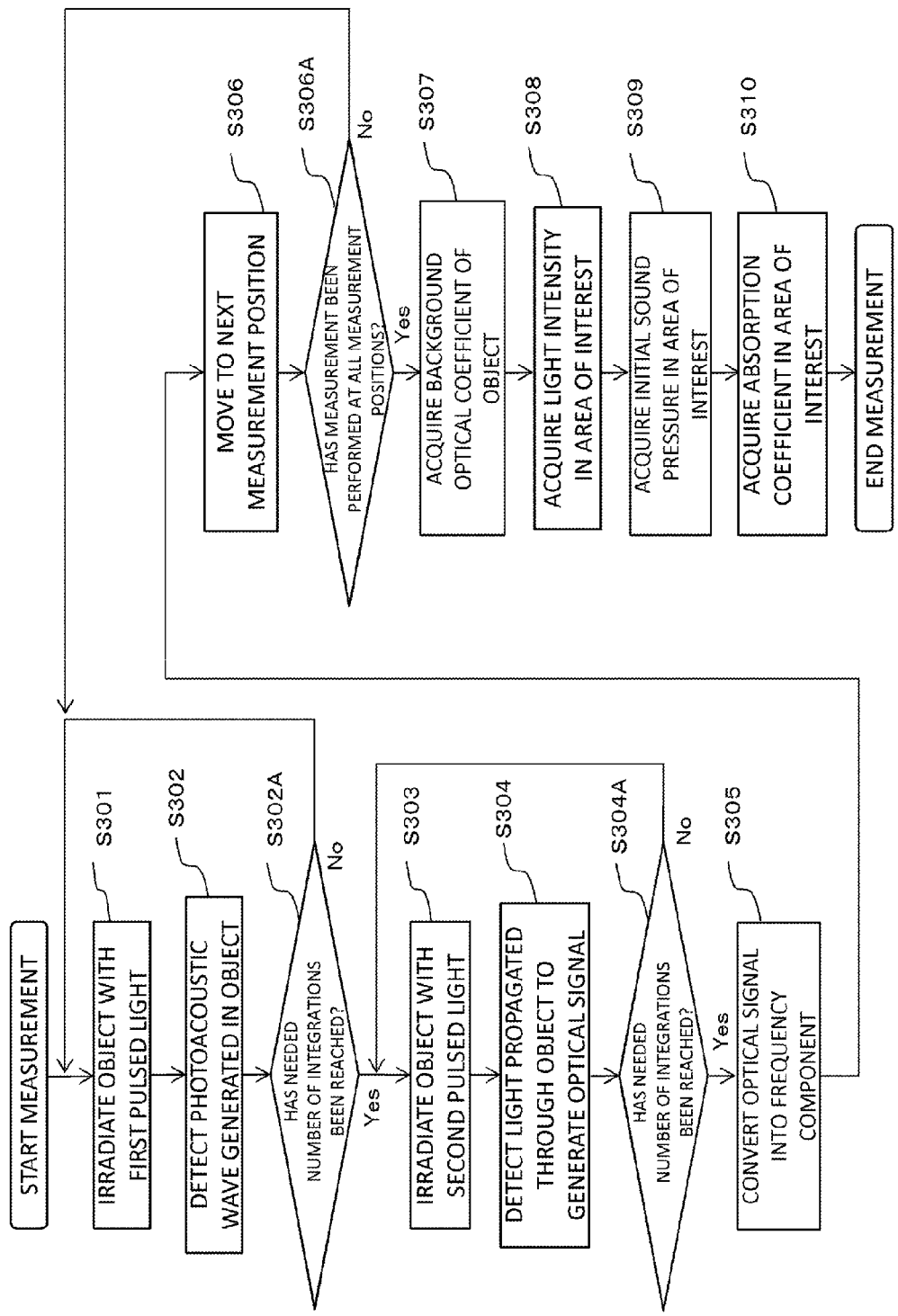
FIG. 13 is a diagram showing the flow of a process executed by the object information acquiring apparatus according to the third embodiment.

Now, the flow of a process executed by an object information acquiring apparatus according to the third embodiment will be described. Steps S301 and S303 in FIG. 13 are identical to steps S101 and S104 according to the first embodiment and will thus not be described below.

Step S302 is a step of receiving a photoacoustic wave generated in the object.

In step S302, the acoustic wave probe 106 receives and converts the photoacoustic wave generated in the region of interest 102 as a result of irradiation with the first pulsed light, into a photoacoustic wave signal. In this case, photoacoustic waves are repeatedly received to integrate signals together until the signals exhibit a sufficient SN ratio value (step S302A).

The final signal resulting from the integration is associated with the measurement position, and then, the resultant signal is sent to the reconstruction unit 1205.

Step S304 is a step of detecting pulsed light used for measurement of the background optical coefficients.

In step S304, the photodetector 107 and the photodetector 1201 detect the pulsed light provided to the object 101 and propagated through the object 101, to generate an optical signal indicative of the transition of the intensity of the detected light. In this case, the pulsed light is repeatedly detected to integrate optical signals together until the optical signals exhibit a sufficient SN ratio value (step S304A).

The final signal resulting from the integration is associated with the measurement position and information identifying the photo-detection unit, and then, the resultant signal is sent to the frequency analysis unit 1203.

Step S305 is a step of converting the generated optical signal into a predetermined frequency component.

In step S305, the frequency analysis unit 1203 converts the optical signal into the frequency domain to acquire the predetermined frequency component. Then, the amplitude decay is acquired using the amplitude of the acquired frequency component and the amplitude of the frequency component of pre-acquired pulsed light. Furthermore, the phase difference is acquired using the phase of the acquired frequency component and the phase of the frequency component of the pulsed light.

Additionally, the frequency analysis unit stores the acquired amplitude decay and phase difference in association with the measurement position and the information identifying the photo-detection unit. Storing the acquired amplitude decay and phase difference allows saving of a larger storage capacity than storing the temporal waveform itself.

Step S306 is a step of moving the measurement position.

In step S306, the moving unit 1202 moves the measurement unit 105 to the next measurement position. Then, at all the measurement positions, steps S301 to S305 are executed (step S306A).

Step S307 is a step of calculating the background optical coefficients of the object.

In step S307, the frequency analysis unit 1203 calculates the distributions of the background optical coefficients of the object 101 in accordance with the phase modulation measurement method using the measurement positions acquired in step S305 and the amplitude decay and phase difference for each photo-detection unit.

Step S308 is a step of acquiring the distribution of light intensity in the region of interest.

In step S308, the light intensity acquiring unit 1204 acquires the distribution of light intensity in the region of interest 102 using the distributions of the background optical coefficients acquired in step S307.

Step S309 is a step of acquiring the distribution of initial sound pressure in the region of interest.

In step S309, the reconstruction unit 1205 reconstructs the signal at each measurement position acquired in step S302 to acquire the distribution of initial sound pressure in the region of interest 102.

All the steps other than the above-described steps are similar to the corresponding steps according to the first embodiment.

According to the third embodiment, obtaining the background optical coefficients of the object 101 in the form of distributions allows the distribution of light intensity in the region of interest 102 to be determined more accurately than the use of average values. This allows the absorption coefficient $\mu_{a\_i}$ to be more accurately determined.

The third embodiment illustrates a case with two photo-detection units and three measurement positions. However, the present invention is not limited to these numbers, and the number of photo-detection units or measurement positions may be increased. This allows the distribution of each background optical coefficient (particularly for spatial resolution) to be more accurately determined. Furthermore, the number of photodetectors may be increased with a single measurement position used, or a single photodetector may be used with the number of measurement positions increased.

Variations

Any method other than the illustrated Fourier transform may be used provided that, for example, the method allows a predetermined frequency component to be extracted from the acquired optical signal.

The description of the embodiments is merely examples used for describing the present invention, and various changes and combination thereof are possible to carry out the invention without departing from the true spirit of the invention. The present invention can also be carried out as a control method for an object information acquiring apparatus that includes at least apart of the above mentioned processing. The above mentioned processing and means can be freely combined to carry out the invention as long as there is no technical inconsistency generated.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-130500, filed on Jun. 21, 2013, and Japanese Patent Application No. 2014-113149, filed on May 30, 2014, which are hereby incorporated by reference herein in its entirety.

What is claimed is:

1. An apparatus comprising:
a light irradiation unit configured to irradiate an object that comprises biological tissue with first pulsed light and second pulsed light;
an acoustic wave probe configured to convert an acoustic wave generated in the object due to the first pulsed light into an acoustic wave signal;
a photo-detection unit configured to convert the second pulsed light which has propagated through the object into a first optical signal having a temporal waveform;
a frequency analysis unit configured to
convert the first optical signal having the temporal waveform into a frequency domain, and
calculate, using a first component of a predetermined frequency of the first optical signal in the frequency domain, optical coefficient data of the object, the optical coefficient data including a background absorption coefficient for an area through which light passes after being provided to the object and before reaching a light absorber in the object and a background scattering coefficient for the area in the object;
a light intensity acquiring unit configured to calculate, using the optical coefficient data of the object, a light intensity distribution of the first pulsed light in the object; and
an information acquiring unit configured to acquire object information, using the acoustic wave signal and the light intensity distribution,
wherein the object information is a distribution of the absorption coefficient in the object, a distribution of concentrations of substances in the object, or a distribution of oxygen saturation in the object.

2. The apparatus according to claim 1, wherein the frequency analysis unit is configured to calculate the optical coefficient data of the object, using an amplitude ratio of the first component and a second component of the predetermined frequency of a second optical signal in frequency domain due to third pulsed light which is not propagated through the object and a phase difference between the first and second components,
wherein a pulse width of the third pulsed light is the same as a pulse width of the second pulsed light.

3. The apparatus according to claim 1, wherein the frequency analysis unit is configured to set the predetermined frequency based on a frequency at which an amplitude or power of a component of the first optical signal in frequency domain is maximized.

4. The apparatus according to claim 1, wherein the frequency analysis unit is configured to set the predetermined frequency based on a frequency corresponding to a reciprocal of a pulse width of the first optical signal, a half cycle or a quarter cycle equal to the half width of the first optical signal, a frequency close thereto, or a harmonic frequency.

5. The apparatus according to claim 1, wherein the photo-detection unit is configured to convert the second pulsed light propagated through the object at a plurality of different positions into a plurality of optical signals.

6. The apparatus according to claim 5, wherein
the frequency analysis unit is configured to calculate, using the plurality of optical signals, a spatial distribution of the optical coefficient data which represents the background absorption coefficient and the background scattering coefficient at plural positions in the object, and
the light intensity acquiring unit is configured to calculate the light intensity distribution, using the spatial distribution of the optical coefficient data.

7. The apparatus according to claim 1, wherein the light irradiation unit is configured to irradiate the object with the second pulsed light having a smaller irradiation area than that of the first pulsed light.

8. The apparatus according to claim 1, wherein the light irradiation unit comprises a plurality of optical members and is configured to switch among the plurality of optical members to individually irradiate the first pulsed light and the second pulsed light.

9. The apparatus according to claim 1, wherein the light irradiation unit is configured to irradiate the object with a single pulsed light as the first pulsed light and the second pulsed light in parallel.

10. The apparatus according to claim 1, wherein a pulse width of the first and second pulsed light is within a range of 10 nanoseconds to 650 nanoseconds at full width at half maximum.

11. The apparatus according to claim 1, wherein a pulse width of the first and second pulsed light is within a range of 100 nanoseconds to 650 nanoseconds at full width at half maximum.

12. The apparatus according to claim 1, wherein the information acquiring unit is configured to calculate, using the acoustic wave signal, an initial sound pressure distribution in the subject, and acquire, using the initial sound pressure distribution and the light intensity distribution, the object information.

13. The apparatus according to claim 1, wherein the background absorption coefficient at plural positions in the object are uniform values and the background scattering coefficient at the plural positions in the object are uniform values.

14. A method for acquiring object information, the method comprising:

a step of controlling a light irradiation unit to irradiate an object that comprises biological tissue with first pulsed light and second pulsed light;

a step of controlling an acoustic wave probe to convert an acoustic wave generated in the object due to the first pulsed light into an acoustic wave signal;

a step of controlling a photo-detection unit to convert the second pulsed light which has propagated through the object into a first optical signal having a temporal waveform;

a step of receiving the acoustic wave signal due to the acoustic wave generated by irradiation of the first pulsed light to the object that comprises the biological tissue;

a step of receiving a first optical signal having the temporal waveform due to the second pulsed light which has propagated through the object;

a step of converting the first optical signal having the temporal waveform into a frequency domain;

a step of calculating, using a first component of a predetermined frequency of the first optical signal in the frequency domain, optical coefficient data of the object;

a step of calculating, using the optical coefficient data, a light intensity distribution, of the first pulsed light, with which the object is irradiated, in the object, the optical coefficient data including a background absorption coefficient for an area through which light passes after being provided to the object and before reaching a light absorber in the object and a background scattering coefficient for the area in the object; and a step of acquiring object information, using the acoustic wave signal and the light intensity distribution, wherein the object information is a distribution of the absorption coefficient in the object, a distribution of concentrations of substances in the object, or a distribution of oxygen saturation in the object.

15. A non-transitory computer readable medium recording a computer program for causing a computer to perform the method according to claim 14.

16. The method according to claim 14, wherein a pulse width of the first and second pulsed light is within a range of 10 nanoseconds to 650 nanoseconds at full width at half maximum.

* * * * *